United States Patent [19]

Albrecht et al.

[11] Patent Number: 5,704,365

[45] Date of Patent: Jan. 6, 1998

[54] USING RELATED SIGNALS TO REDUCE ECG NOISE

[75] Inventors: Paul Albrecht, Bedford; Jeffrey M. Arnold, Wellesley; Neil Judell, Andover; Richard J. Cohen, Waban, all of Mass.

[73] Assignee: Cambridge Heart, Inc., Bedford, Mass.

[21] Appl. No.: 557,883

[22] Filed: Nov. 14, 1995

Related U.S. Application Data

[63] Continuation-in-part of Ser. No. 339,050, Nov. 14, 1994, abandoned, Ser. No. 339,032, Nov. 14, 1994, abandoned, and Ser. No. 379,375, Jan. 26, 1995.

[51] Int. Cl.⁶ .................................................. A61B 5/0472
[52] U.S. Cl. ................................................ 128/702; 128/901
[58] Field of Search ........................... 128/696, 698–700, 128/702, 704, 705, 733, 734, 901

[56] References Cited

U.S. PATENT DOCUMENTS

| | | | |
|---|---|---|---|
| 3,566,233 | 2/1971 | Kahn | 324/71 |
| 4,084,583 | 4/1978 | Hjort . | |
| 4,141,351 | 2/1979 | James et al. . | |
| 4,211,237 | 7/1980 | Nagel | 128/698 |
| 4,245,643 | 1/1981 | Benzing, III et al. . | |
| 4,321,932 | 3/1982 | Francis | 128/696 |
| 4,337,776 | 7/1982 | Daly et al. . | |
| 4,421,121 | 12/1983 | Whisler et al. | 128/731 |
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,519,396 | 5/1985 | Simon et al. | 128/705 |
| 4,556,962 | 12/1985 | Widrow et al. | 367/45 |
| 4,583,549 | 4/1986 | Manoli | 128/640 |
| 4,630,204 | 12/1986 | Mortara | 364/417 |
| 4,732,157 | 3/1988 | Kaplan et al. | 128/696 |
| 4,751,931 | 6/1988 | Briller et al. | 128/700 |
| 4,760,540 | 7/1988 | Yuen | 364/724 |
| 4,781,201 | 11/1988 | Wright et al. | 128/671 |
| 4,783,660 | 11/1988 | Pierce | 342/101 |
| 4,802,491 | 2/1989 | Cohen et al. | 128/702 |
| 4,870,341 | 9/1989 | Pihl et al. | 324/57 R |
| 4,899,750 | 2/1990 | Ekwall . | |
| 4,917,099 | 4/1990 | Stice | 128/696 |
| 4,945,917 | 8/1990 | Akselrod et al. | 128/696 |
| 4,955,383 | 9/1990 | Faupel | 128/653 R |
| 4,974,598 | 12/1990 | John | 128/696 |
| 4,979,110 | 12/1990 | Albrecht et al. . | |
| 4,993,423 | 2/1991 | Stice | 128/696 |
| 5,010,888 | 4/1991 | Jadvar et al. | 128/696 |
| 5,020,538 | 6/1991 | Morgan et al. | 128/653 R |
| 5,020,541 | 6/1991 | Marriott | 128/723 |
| 5,146,926 | 9/1992 | Cohen | 128/710 |

(List continued on next page.)

OTHER PUBLICATIONS

Mortara, D.W., "Source Consistency Filtering—A New Tool for ECG Noise Reduction," Computers in Cardiology, 1991, pp. 125–128.

(List continued on next page.)

*Primary Examiner*—Jeffrey R. Jastrzab
*Attorney, Agent, or Firm*—Fish & Richardson P.C.

[57] ABSTRACT

A method of reducing noise in a signal that represents a physiologic process includes obtaining multiple input signals, measuring a relationship between noise content of the input signals, and combining the input signals in consideration of the measured relationship to produce an output signal having low noise content. The multiple input signals may include, for example, two or more primary physiologic input signals or one or more primary physiologic input signals and two or more secondary input signals that represent noise. The method may further include dividing one or more ECG input signals and secondary input signals into set of segments, where each set of segments represents a beat of the ECG signal, measuring a relationship between noise content of corresponding points from successive sets of segments, and combining the input signals based on the measured relationship.

58 Claims, 17 Drawing Sheets

U.S. PATENT DOCUMENTS

| | | | |
|---|---|---|---|
| 5,148,812 | 9/1992 | Verrier et al. | 128/704 |
| 5,184,620 | 2/1993 | Cudahy et al. | 128/639 |
| 5,188,116 | 2/1993 | Pommrehn et al. | 128/696 |
| 5,197,479 | 3/1993 | Hubelbank et al. | 128/696 |
| 5,209,237 | 5/1993 | Rosenthal | 128/698 |
| 5,237,995 | 8/1993 | Cano | 128/640 |
| 5,305,746 | 4/1994 | Fendrock | 128/641 |
| 5,341,811 | 8/1994 | Cano | 128/696 |
| 5,372,139 | 12/1994 | Holls et al. | 128/698 |
| 5,421,342 | 6/1995 | Mortara | 128/696 |
| 5,437,285 | 8/1995 | Verrier et al. | 128/702 |
| 5,560,370 | 10/1996 | Verrier et al. | 128/705 |

OTHER PUBLICATIONS

Wel, Daming et al., "A New Method for Reducing Signal-Overlapping Noise in Standard Electrocardiogram," Proceedings of Computers in Cardiology, London, U.K., 1993, Sep. 5-8, 1993, pp. 795-798.

Cano, Gerald G. et al., "Enhancement of Low-Level ECG Components in Noise With Time-Sequenced Adaptive Filtering," Journal of Electrocardiology, vol. 23 Supplement, Proceedings of the 15th Annual ISCE Conference, Apr. 22-27, 1990, pp. 176-183.

Mortara, David W., "Source Consistency Filtering, Application To Resting ECGs," Journal of Electrocardiology, vol. 25 Supplement, Proceedings of the 17th Annual ISCE Conference, May 2-7, 1992, pp. 200-206.

Adam et al., "Estimation of Ventricular Vulnerability to Fibrillation Through T-Wave Time Series Analysis," Computers in Cardiology, pp. 307-310 (1981).

Adam et al., "Fluctuations in T-Wae Morphology and Susceptibility to Ventricular Fibrillation," J. Electrocardiology 17(3), pp. 209-218 (1984).

Callaerts et al., "An On-Line Adaptive Algorithm for Signal Processing Using SVD," Signal Processing III, I.T. Young et al. (editors), Elsevier Science Publishers B.V., North-Holland, pp. 953-956 (1986).

Callaerts et al., "An Adaptive On-Line Method for the Extraction of the Complete Fetal Electrocardiogram from Cutaneous Multilead Recordings," J. Perinat. Med., vol. 14, No. 6, New York, pp. 421-433 (1986).

Cano et al., "Enhancement of Low-Level ECG Components in Noise With Time-Sequenced Adaptive Filtering," J. Electrocardiology, vol. 23 Supplement, pp. 176-183 (1990).

Mortara, "Source Consistency Filtering—Application to Resting ECGs," J. Electrocardiology, vol. 25 Supplement, pp. 200-206 (1992).

Mortara, "Source Consistency Filtering—A New Tool for ECG Noise Reduction," IEEE, pp. 125-128 (1992).

Rosenbaum et al., "Electrical Alternans and Vulnerability to Ventricular Arrhythmias," New England Journal of Medicine 330, pp. 235-241 (1994).

Salerno et al., "Ventricular Arrhythmias During Acute Myocardial Ischaemia in Man. The Role and Significance of R-ST-T Alternans . . . ," European Heart Journal 7 (Supp. A), pp. 63-75 (1986).

Shvartsman et al., "Multichannel Signal Processing Based on Logic Averaging," IEEE Transactions on Biomedical Engineering, vol. BME-29, No. 7, pp. 531-536 (1982).

Smith et al., "Electrical Alternans and Cardiac Electrical Instability," Circulation, vol. 77, No. 1, 110-121 (1988).

Smith et al., "Subtle Alternating Electrocardiographic Morphology as an Indicator of Decreased Cardiac Electrical Stability," Computers in Cardiology, pp. 109-112 (1985).

Widrow, "Adaptive Interference Canceling," Adaptive Signal Processing, Applications Part IV, Chap. 12, Prentice-Hall, Englewood Cliffs, NJ, pp. 302-367 (1985).

Zimmerman et al., "Beat-to-Beat Detection of Ventricular Late Potentials with High-Resolution Electrocardiography," American Heart Journal, vol. 121, No. 2, Part 1, pp. 576-585 (1991).

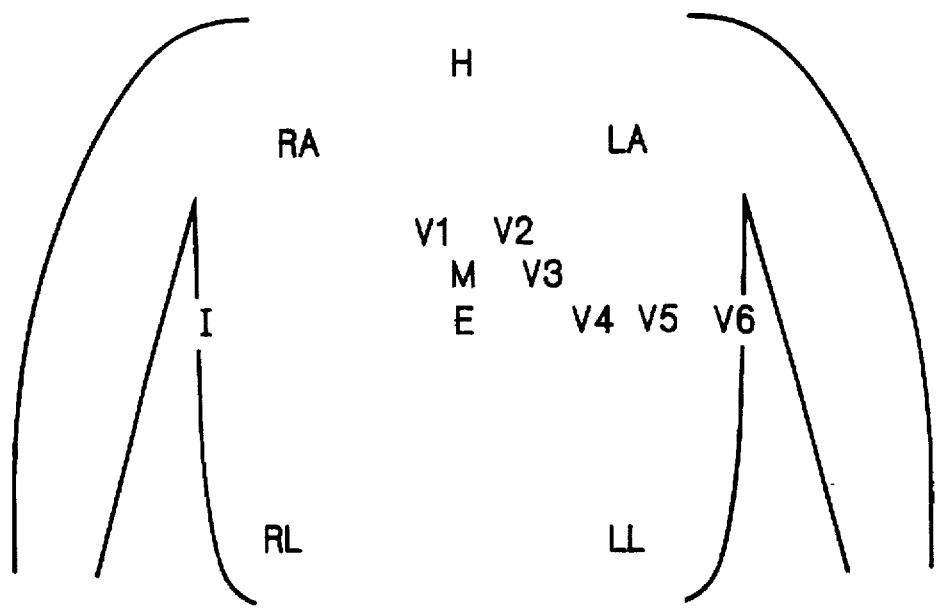

FIG. 3

| Electrode Name | Electrode Location | Type | Available Signals |
|---|---|---|---|
| RL | R. ILLIAC CREST | STANDARD | (DRIVEN GROUND) |
| RA | RIGHT SHOULDER | STANDARD | (REFERENCE) |
| LA | L. SHOULDER | STANDARD | LA |
| LL(F) | L. ILLIAC CREST | MULTIPLE | LLa, LLb, LLc, LLi |
| V1 | V1 | STANDARD | V1 |
| V2 | V2 | STANDARD | V2 |
| V3 | V3 | STANDARD | V3 |
| V4(C) | V4 | MULTIPLE | V4, V4a, V4i |
| V5 | V5 | STANDARD | V5 |
| V6(A) | V6 | MULTIPLE | V6, V6a, V6b, V6i |
| I | R. V6 POSITION | MULTIPLE | I, Ia, Ib, Ii |
| H | BELOW NECK | MULTIPLE | H, Ha, Hi |
| E | BETWEEN A & I | MULTIPLE | E, Ea, Ei |
| M | BACK | MULTIPLE | M, Ma, Mb, Mi |

FIG. 4

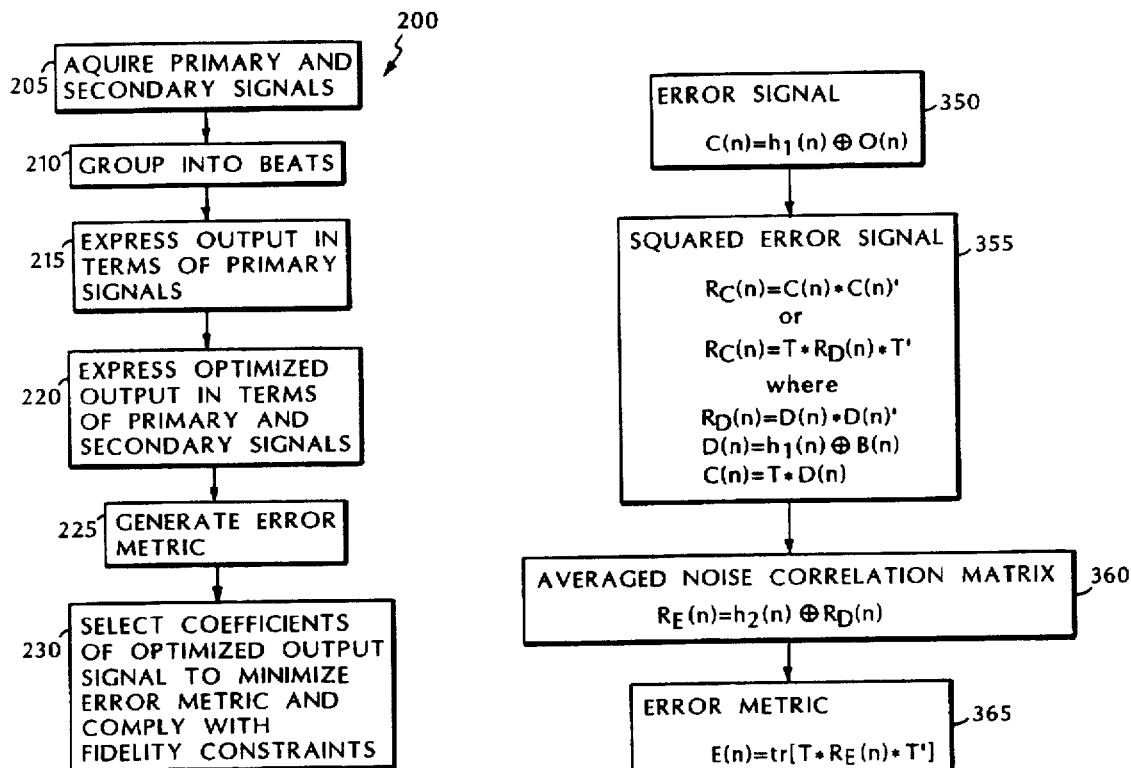

| MATRIX | SIZE | DESCRIPTION |
|---|---|---|
| $B(n)$ | $L \times M$ | Beat matrix containing the samples of the nth beat. |
| $F$ | $K \times L$ | Matrix of coefficients defining the output signal $S(n)$ from $B(n)$. |
| $T$ | $K \times L$ | Matrix of coefficients defining the output signal $O(n)$ from $B(n)$. |
| $S(n)$ | $K \times 1$ | The output signal computed as $S(n) = F*B(n)$. |
| $O(n)$ | $K \times 1$ | The optimized output signal computed as $O(n) = L*B(n)$. |
| $C(n)$ | $K \times 1$ | The optimized output signal computed as $C(n) = h_1(n) \otimes O(n)$. |
| $R_C(n)$ | $L \times L$ | Correlation matrix which is the "square" of $C(n)$: $R_C(n) = C(n)*C'(n)$. |
| $D(n)$ | $L \times L$ | A filtered version of $B(n)$ that retains only frequency content to be eliminated from the output signal: $D(n) = h_1(n) \otimes B(n)$. |
| $R_D(n)$ | $L \times L$ | Correlation matrix that is the "square" of $D(n)$: $R_D(n) = D(n)*D'(n)$. |
| $R_E(n)$ | $L \times L$ | Correlation matrix obtained by taking a weighted average of $R_D(n)$: $R_E(n) = h_2(n) \otimes R_D(n)$. |
| $E(n)$ | $1 \times 1$ | Error metric for the nth beat. Computed as the trace of $R_E(n)$. May include other terms. |
| $A(n)$ | $L \times M$ | Mean beat computed as a weighted average of $B(n)$: $A(n) = h_3(n) \otimes B(n)$. |
| $R_A(n)$ | $L \times L$ | Correlation matrix that is the "square" of $A(n)$: $R_A(n) = A(n)*A'(n)$. |

FIG. 6A

| FILTER | SIZE | DESCRIPTION |
|---|---|---|
| $h_1(n)$ | | Filter that creates $D(n)$ from $B(n)$; passes the frequency bands that are to be removed from the output. |
| $h2(n)$ | | Filter that creates $R_E(n)$ from $R_D(n)$; takes a weighted average of $R_D(n)$ over a range of beats. |
| $h_3(n)$ | | Filter that creates $A(n)$ from $B(n)$; passes the frequency bands that are to be preserved in the output; creates a weighted average over a range of beats. |

FIG. 6B

| Row | Signal | Row | Signal |
|---|---|---|---|
| 1 | LA | 17 | V6i |
| 2 | LL | 18 | I |
| 3 | LLa | 19 | Ia |
| 4 | LLb | 20 | Ib |
| 5 | LLc | 21 | Ii |
| 6 | LLi | 22 | H |
| 7 | V1 | 23 | Ha |
| 8 | V2 | 24 | Hi |
| 9 | V3 | 25 | E |
| 10 | V4 | 26 | Ea |
| 11 | V4a | 27 | Ei |
| 12 | V4i | 28 | M |
| 13 | V5 | 29 | Ma |
| 14 | V6 | 30 | Mb |
| 15 | V6a | 31 | Mi |
| 16 | V6b | 32 | Resp |

$b(n) =$ $$F_{xyz} = \begin{bmatrix} F_x \\ F_y \\ F_z \end{bmatrix}$$

$$D_{xyz}(n) = F_{xyz} B(n)$$
$$D_{V4}(n) = F_{V4} B(n)$$

FIG. 25

| Col | Signal | $F_X$ | $F_X$ | $F_X$ | $F_X$ |
|---|---|---|---|---|---|
| 1 | LA | | | | |
| 2 | LL | | 0.655 | | |
| 3 | LLa | | | | |
| 4 | LLb | | | | |
| 5 | LLc | | | | |
| 6 | LLi | | | | |
| 7 | V1 | | | | |
| 8 | V2 | | | | |
| 9 | V3 | | | | |
| 10 | V4 | 0.171 | | -0.231 | 1.000 |
| 11 | V4a | | | | |
| 12 | V4i | | | | |
| 13 | V5 | | | | |
| 14 | V6 | 0.610 | | 0.133 | |
| 15 | V6a | | | | |
| 16 | V6b | | | | |
| 17 | V6i | | | | |
| 18 | I | -0.781 | | -0.264 | |
| 19 | Ia | | | | |
| 20 | Ib | | | | |
| 21 | Ii | | | | |
| 22 | H | | -1.00 | | |
| 23 | Ha | | | | |
| 24 | Hi | | | | |
| 25 | E | | | -0.734 | |
| 26 | Ea | | | | |
| 27 | Ei | | | | |
| 28 | M | | 0.345 | 0.736 | |
| 29 | Ma | | | | |
| 30 | Mb | | | | |
| 31 | Mi | | | | |
| 32 | Resp | | | | |

USING RELATED SIGNALS TO REDUCE ECG NOISE

CROSS REFERENCE TO RELATED APPLICATIONS

This application is a continuation-in-part of U.S. application Ser. No. 08/339,050, entitled "Improved Method and Apparatus for Assessing Cardiac Electrical Stability" and filed Nov. 14, 1994 now abandoned; a continuation-in-part of U.S. application Ser. No. 08/339,032, entitled "Measuring a Physiologic Signal" and filed Nov. 14, 1994 now abandoned, and a continuation-in-part of U.S. application Ser. No. 08/379,375, entitled "Measuring and Assessing Cardiac Electrical Stability" and filed Jan. 26, 1995. The disclosures of each of these applications is incorporated herein by reference.

BACKGROUND OF THE INVENTION

The invention relates to reducing noise in measurement of a physiologic signal.

Accurate measurement of physiologic signals is extremely important in many diagnostic and therapeutic applications. For example, it has been recently discovered that alternans, a subtle beat-to-beat change in the repeating pattern of an electrocardiogram (ECG) waveform can be indicative of electrical instability of the heart and increased susceptibility to sudden cardiac death. Alternans results in an ABABAB . . . pattern of variation of waveform shape between successive beats in an ECG waveform, and the level of cardiac stability is taken as a characterization of an individual's cardiac electrical stability.

The physiologic signal underlying an ECG waveform may be obtained through electrodes attached to a patient's chest. Typically, the electrodes include an electrically conductive gel that contacts the patient's skin and detects electrical signals produced by the patient's heart. The detected signals are then transmitted to ECG circuitry for processing and display.

Referring to FIG. 1, an ECG waveform for a single beat is typically referred to as a PQRST complex. Briefly, the P wave appears at initiation of the beat and corresponds to activity in the atria, while the QRST complex follows the P wave and corresponds to ventricular activity. The QRS component represents the electrical activation of the ventricles, while the T wave represents the electrical recovery thereof. The ST segment is a relatively quiescent period. In humans, it has been found that the T wave is the best interval of the ECG complex for detecting alternans. That is, a level of variation in the T waves of alternating beats is the best indicator of a patient's level of alternans.

Typically, the amplitude of an ECG waveform is measured using an isoelectric point as the zero voltage reference. The isoelectric point is measured during the PQ interval between the P wave and QRS complex. The PQ interval is a good approximation to a zero ECG level because there is no major electrical activity in the heart at that time. It is important to note that the ECG waveform has DC content and that the zero ECG level does not necessarily correspond to zero volts. Thus, any high pass filtering of the waveform will offset the isoelectric point.

While an ECG waveform typically has a QRS amplitude measured in millivolts, an alternans pattern of variation with an amplitude on the order of a microvolt may be clinically significant. Accordingly, the alternans pattern may be too small to be detected by visual inspection of the electrocardiogram and often must be detected and quantified electronically. Such electronic detection and quantification of the alternans pattern is further complicated by the presence of noise in the ECG waveforms, as the noise may result in beat-to-beat variations in the ECG waveforms that have a larger magnitude than the alternans pattern of variation.

The noise in an ECG signal can be classified into three categories: baseline noise generated in the electrode, physiologic noise, and external electrical noise. The baseline noise is low frequency noise that appears as an undulating baseline upon which the ECG rides. Baseline noise is attributable to motion and deformation of the electrode and its associated gel, and results from low frequency events such as patient respiration and patient motion. As a result, the magnitude of baseline noise tends to increase with exercise. However, many important ECG measurements must be made during exercise. Typically, the frequency content of baseline noise is below 2 Hz.

Physiologic noise results from other physiologic processes within the patient that interfere with the ECG signal, with skeletal muscle activity being the most common source of physiologic noise. The electrical activity of the skeletal muscles creates potentials that are additive with respect to the potentials created by the heart. The frequency content of the skeletal muscle signals is comparable to the frequency content of the QRS complex, and is typically greater than 10 Hz. When measuring T wave alternans, additional physiologic noise may result from changes in the position of the heart due to respiration or from changes in the projection of the electrical potential from the heart to the skin surface due to thoracic conductivity changes arising from the inflation and deflation of the lungs with respiration.

External electrical noise results, for example, from ambient electromagnetic activity in the room, electrode cable motion, and variations in amplifiers or other components of the ECG circuitry. External electrical noise may be eliminated or reduced through the use of high quality components and through the reduction of ambient electromagnetic activity by, for example, deactivating high power equipment.

Noise reduction is of particular importance in applications that attempt to measure low level ECG features such as ST segment changes, P waves, or the fetal ECG, and of even more importance in applications that attempt to measure microvolt level features of the ECG, such as electrical alternans, His-Purkinje activity, and late potentials such as might be measured by a signal averaged ECG (SAECG). Noise in the ECG waveform can easily mask the presence of alternans. The noise can also mimic the presence of alternans where there is none. For example, if a patient is breathing at one-half or one-third of the heart rate, the respiration may introduce a harmonic signal having the ABABAB . . . pattern of alternans. Similarly, motion that repeats with some periodicity, such as that resulting from exercise, can create electrode noise with a similar pattern. Furthermore, noise resulting from different sources, such as respiration and electrode noise, can interact and produce new periodicities, one of which may mimic alternans. For all of these reasons, the reduction of interfering noise is of paramount importance for the measurement of alternans.

ECG noise reduction strategies have drawn on a variety of mathematical methods to reduce the noise. The strategies can be grouped into several categories, including temporal filtering of one dimensional input signals, spatial filtering of input signals, adaptive filtering of input signals using a reference input, and source consistency filtering of input signals.

The simplest form of temporal filter is a linear filter, such as a low-pass, high-pass, or band-pass filter. Some linear filters have been designed with a time-varying frequency response. For example, the filter may process the QRS complex differently from the rest of the ECG complex. Temporal filters also include non-linear filters and cubic spline filters. The cubic spline filter is a mathematical methodology for approximating (and then subtracting out) the baseline noise using only measurements of the isoelectric point measured in the PQ interval. The methodology uses a third order, discrete time difference equation having parameters that are determined from the values of the isoelectric points. The method can be loosely described as fitting a cubic equation to the isoelectric point of four beats and subtracting the cubic prediction in the interval between the isoelectric points of the second and third beats.

Temporal filtering can exploit the repeating nature of the ECG complex. The average of multiple ECG complexes can be used to remove noise while preserving the repeating ECG component. As described in U.S. Pat. No. 5,348,960, singular value decompositions of the ECG complexes can be used to identify the temporal and waveform eigenvectors that account for the dominant features of the ECG complexes. The waveform eigenvectors correspond to the principal components of the beat-to-beat fluctuations. By reconstructing the original ECG complexes using only a subset of the dominant eigenvectors, the ECG complexes may be reproduced while noise is suppressed.

With spatial filtering, ECG signals are represented as an average of multiple input signals. Typically, spatial filtering techniques assume that the ECG signal is present to the same degree in all input signals so that the input signals can be directly combined. When the input signals cannot be combined directly, they can be characterized by the spatial eigenvectors of the singular value decomposition of the input signals. As described in U.S. Pat. No. 5,348,960, the use of spatial eigenvectors permits the original space of input signals to be reduced to a much smaller subspace. The spatial eigenvectors can be combined with the temporal or waveform eigenvectors.

Adaptive filtering uses a reference signal in combination with an input signal to estimate a filter that removes the noise from the input signal. Adaptive filters are intended to operate with reference and input signals which are chosen to be very similar to each other. With each new sample, an adaptive filter estimates and updates a filter response to minimize an error signal that is the difference between the filtered input signal and the reference signal. An adaptive filter can be used as a noise canceller by defining the reference signal as the component to be cancelled. For example, U.S. Pat. No. 4,793,361 describes a technique that attempts to enhance P-waves by cancelling the QRS complex. The P-wave filter functions to reproduce the dominant component (i.e., the QRS complex), which leaves the P-wave as a major component of the error signal. The error signal is then used as the P-wave signal.

Source consistency filtering is closely related to spatial filtering, with the difference being that source consistency filtering recognizes that the correlation between input signals is the result of an underlying single ECG source generator. A source consistency filter described by Mortara in U.S. Pat. No. 5,421,342 compares the value of an ECG signal with a predicted value for that signal, and generates the predicted value using other ECG signals. The predicted value is based on a least squares estimate derived from the covariance matrix of the input signals. A filtered ECG signal is formed by linearly combining the observed ECG signal and its predicted value.

Another approach is discussed by Devlin et al. in "Detecting Electrode Motion Noise in ECG Signals by Monitoring Electrode Impedance", *Computers in Cardiology*, 1984. In the system described by Devlin et al., an ECG signal produced by an electrode is collected simultaneously with a signal related to the impedance of the electrode/skin interface of the electrode. The impedance signal is then used to estimate noise in the ECG signal due to electrode motion. Finally, the estimated noise is employed in an algorithm for reducing the occurrence of false positive alarms in an automated arrhythmia detector. According to the algorithm, an estimate of the noise in the ECG signal is made by determining a transfer function relating the impedance signal to the ECG signal using a minimum mean square estimation algorithm and applying the transfer function to the impedance signal to provide the estimate of the noise. Finally, a peak noise-to-signal ratio is determined by subtracting the noise estimate from the ECG signal to produce a "noise free" ECG signal from which an RMS value is computed, calculating RMS values of the noise estimate for time windows of the noise estimate, selecting the largest RMS value as the peak noise signal, and dividing the peak noise signal by the RMS value of the "noise free" ECG signal to produce the ratio. Devlin et al. also note that subtracting the noise estimate from the ECG channel as a means of improving the quality of the ECG channel had been explored.

SUMMARY OF THE INVENTION

The invention provides an improved technique for reducing noise in physiologic signals such as ECG signals. The noise-reduction technique derives from the realization that signals representative of a physiologic process and signals representative of obscuring noise appear differently to different types of sensors or to sensors at different locations and can therefore be accurately separated. In essence, the noise-reduction technique employs seemingly redundant signals along with signals that are related to obscuring noise to produce a signal from which the noise content has been reduced.

The noise-reduction technique differs from the spatial filtering and source consistency filtering techniques described above in that it considers the relationship of the noise content of the input signals and finds the combination of input signals that minimizes the noise while preserving the desired features of the signal. The noise-reduction technique does not seek to blend an original signal with a prediction for that signal. Thus, unlike the signal produced by the source consistency filter, the signal produced by the noise-reduction technique is not a weighted average of an original signal and one or more predicted signals. Instead, the noise-reduction technique uses each signal as a vector projection of the underlying ECG generator onto the body surface and combines the signals in a manner that optimally reduces the noise while preserving the net vector direction of the ECG generator.

The noise-reduction technique is implemented using a generalized procedure that begins by acquiring primary and secondary input signals. Primary signals are defined as signals that include part or all of a desired signal from a physiologic process and obscuring noise from one or more noise processes. Secondary signals are defined as signals that contain noise which may be related to the noise in the primary signals. In some instances, only primary signals may be acquired.

Once the primary and secondary signals are acquired, a desired output signal is defined as a combination of one or more primary signals. (The term "combination" is used to refer to any mathematical operation that defines a signal in terms of one or more other signals.) The desired output signal includes a desired component and noise. A particular embodiment defines the desired output signal as a linear combination of the primary signals. The manner in which each primary signal contributes to the desired output signal is defined with specificity.

Some or all of the input signals may be processed by transformations and/or combinations prior to their use in modifying the ECG signal. A signal may be created by lagging, filtering, or generally transforming another signal. For example, the impedance signals may be filtered to retain only frequencies known to be related to the baseline noise in the ECG signal. The processing may be general, such as raising the signals to a power, or may involve projection onto other vectors, or decomposition and reconstruction using wavelets. The processed signal may be used to replace part or all of the original signal, or may be included as an additional one of the input signals. One advantage of this generalization is that is permits a linear model approach to incorporate more complicated or even non-linear models.

Next, a model of a low-noise output signal that approximates the desired component of the desired output signal is defined as a combination of the primary and secondary input signals. At this point in the noise-reduction procedure, the parameters of the low-noise output signal (i.e., the degree to which each primary or secondary signal contributes to the low-noise output signal) are left as variable amounts. The model, referred to as a noise reduction model, is based on the realization that there are underlying models (whether explicit or empirical) for the generation and characteristics of the physiologic signal and the obscuring noise. The structure of these models acts as a guide in selecting which primary and secondary signals to acquire, and in defining the noise reduction model for creating the low-noise output signal from the input signals.

A noise measure, or error metric, that quantifies the noise content of the low-noise output signal for different parameter values of the noise reduction model. Additional fidelity constraints may also be defined. The fidelity constraints assure that the desired signal is preserved in the low-noise output signal. The fidelity constraints can include either direct measures of desired signal content in the low-noise output signal or direct constraints on the parameters of the low-noise output signal, or both.

Finally, parameters of the noise reduction model that minimize the noise measure while satisfying the fidelity requirements are selected using all or some of the primary and secondary signals. The selected parameters are then applied using the noise reduction model to produce the low-noise output signal. The selected parameters may be applied to an interval of the low-noise output signal that is the same, shorter or longer than, or offset in time from, the interval of input signals used to select the parameters.

In a simple example of the noise-reduction procedure, a low-noise output signal is produced using a single primary signal and a single secondary signal. The primary signal is an ECG signal produced by an electrode, and the secondary signal provides a measure of the impedance of the electrode. The desired output signal is the ECG signal at the surface of a patient's skin. However, in addition to the desired ECG signal, the primary signal includes baseline noise. For this reason, noise reduction is performed to separate the baseline noise from the ECG signal and to produce a low-noise output signal that reflects only the ECG signal.

Variations in the impedance of an electrode reflect the baseline noise introduced into the signal that the electrode produces. As noted above, baseline noise is attributable to motion and deformation of the electrode and its associated gel, and results from low frequency events such as patient respiration and patient motion. In particular, it has been found that baseline noise results from changes in the structure of the gel-skin interface due from acceleration and compression forces on the gel and on the gel-skin interface. For example, respiration is associated with periodic expansion and contraction of the chest cavity. This periodic motion of the chest cavity results in periodic expansion and contraction of the gel-skin interface due to motion of the skin underlying the interface. The gel-skin interface and the gel-to-connector interface create a battery-like potential in which the gradient of the ions across the two sides of the interface is balanced by the potential difference across the interface due to the imbalance of these charged ions. The ion balance, and hence the potential across the interface, is sensitive to changes in the geometry of the interface. As a result, when the gel is moved or compressed relative to the interface, the ion balance changes and currents flow across the interface. These currents change the electrical potential across the interface. The primary signal includes an ECG-related potential summed with the potential across the electrode interface. Thus, variations in the interface potential affect the primary signal and constitute baseline noise.

Deformation of the electrode due to the acceleration and compression of the electrode gel results in variations in the impedance of the electrode and the gel-skin interface. Because they come from the same source, the impedance variation is directly related to the baseline noise, and may be used as an indicator of the noise. Accordingly, the effects of baseline noise may be eliminated or reduced by modifying the ECG signal (the primary signal) in view of the monitored impedance (the secondary signal).

In the simple example of the noise-reduction technique, the impedance of an electrode (the secondary signal) is measured simultaneously with the primary signal produced by the electrode. The impedance measurement is produced by applying one or more high frequency signals to the electrode and measuring the output of the electrode. The applied frequencies are selected to be well above the expected frequency of the ECG signal so that the high frequency signals do not interfere with the ECG signal. For example, signals having frequencies of 28 kHz and 56 kHz may be employed. At these frequencies, the impedance of the electrodes is primarily attributable to the capacitance of the electrode. Lower or higher frequencies could also be employed.

Using the noise-reduction technique, the low-noise output signal is modelled as a combination of the primary signal and the secondary signal. In addition, an error metric is also defined. The error metric represents a specific time range of the primary signal. The time range of the error signal that is used in computing the metric may depend on, and may vary from, the time range to which the error metric applies.

When the model for the low-noise output signal is defined, it includes one or more variable parameters. Once the error metric is defined, the values of the model parameters are assigned based on the error metric. For example, the parameters may be assigned values that cause the error metric to have a low value, and may be varied as the error metric varies. Depending on the application, the values of the parameters may be computed in real time, near real time, or retrospectively. Thereafter, the low-noise output signal is generated using the values assigned to the parameters.

It also has been determined that the relationship between baseline noise for an electrode and the impedance measured for that electrode may be imperfect. For example, motion that influences the baseline noise of an electrode may not influence the impedance of the electrode to the same extent. However, the motion may influence the impedances of other electrodes in a way that provides a more complete representation of the noise. This provides motivation to use other impedances from other electrodes that may capture additional information related to baseline noise. In addition, trans-thoracic impedance may be measured as a proxy for baseline noise resulting from respiration. Transthoracic impedance provides a measurement which relates to the motion of the chest because it is strongly modulated by respiration. Chest motion causes motion of the electrodes and hence is related to baseline noise.

In a more complicated example of the noise-reduction technique, multiple primary signals and multiple secondary signals are used to produce a single low-noise output signal. In particular, a single low-noise ECG signal is produced using redundant ECG signals and multiple impedance signals. In the example, the desired output signal is an ECG signal defined as the difference between signals produced by two electrodes. To produce the redundant ECG signals, the electrodes are implemented using multi-segment electrodes that produce multiple signals, and the desired output signal is defined as the difference between the signals at the center segments of the two electrodes. The segments of the multi-segment electrodes may be biased to different degrees, or otherwise modified, so that the signals produced by the segments are affected differently by the baseline noise. Three impedance signals are employed. The first two impedance signals correspond to the impedances of segments of the two electrodes such as the center segments. The third impedance signal corresponds to transthoracic impedance.

A noise suppression model is defined to express the low-noise output signal as a combination of the redundant ECG signals and the impedance signals. An error metric and fidelity constraints are then defined. In this example, a useful fidelity constraint is that the low-noise output signal, when considered over multiple beats, is comparable to the desired output signal (i.e., the average difference between the center segments). Finally, parameters for the noise suppression model are selected so as to minimize the error metric and to comply with the fidelity requirements.

In a variation of the basic technique, low-noise output signals for use in measuring alternans are produced using a two-stage noise-reduction technique. Input signals are produced using a set of multi-segment electrodes and a set of standard electrodes. In a first noise-reduction stage, the input signals are processed according to the noise-reduction technique to produce a set of low-noise electrode signals representing low noise versions of the signals from each electrode. In particular, the noise-reduction technique is employed to produce low-noise output signals for each multi-segment electrode using the redundant ECG signals from the segments of the electrode along with impedance signals for each of the multi-segment electrodes and a trans-thoracic impedance signal representative of respiration. Similarly, the noise-reduction technique is employed to produce a low-noise output signal for each of the standard electrodes using the ECG signal for the standard electrode and the multi-segment electrode and trans-thoracic impedance signals.

The low-noise electrode signals produced in the first noise-reduction stage are used as input signals for a second noise-reduction stage. In the second stage, the noise-reduction technique is applied to produce a set of low-noise signals from the low-noise electrode signals. This set of low-noise signals, is then used to measure alternans.

In one aspect, generally, the invention features reducing noise in a signal that represents a physiologic process by obtaining multiple input signals, measuring a relationship between noise content of the input signals, and combining the input signals in consideration of the measured relationship to produce an output signal having low noise content.

Preferred embodiments of the invention may include one or more of the following features. The multiple input signals may include, for example, two or more primary physiologic input signals, one or more primary physiologic input signals and two or more secondary input signals that represent noise. Similarly, the multiple input signals may include one or more ECG input signals and one or more secondary input signals that represent noise, and the method may include dividing the ECG input signals and secondary input signals into set of segments, where each set of segments represents a beat of the ECG signal. Thereafter, a relationship between noise content of corresponding points from successive sets of segments may be measured for use in combining the signals.

The method may further include defining a desired output signal as a combination of one or more of the input signals, modelling a low-noise output signal that approximates the desired output signal as a combination of two or more of the input signals, with the model of the low-noise output signal including variable parameters that represent the relative contribution made to the low-noise output signal by each of the two or more input signals. Thereafter, based on the relationship between noise content of the input signals, an error metric that represents noise content in the low-noise output signal is produced. Finally, values of the variable parameters that cause the error metric to satisfy a predetermined condition are determined and the input signals are combined to produce the low-noise output signal using the determined values of the variable parameters.

Input signals may be obtained using electrodes applied to a patient's skin, and additional input signals may represent impedances associated with the electrodes. Similarly, multiple input signals may be obtained using segments of a multi-segment electrode. One or more of the input signals may be representative of respiration by a patient.

Values of the variable parameters may be determined so that the values reduce or minimize the value of the error metric. Values may be determined so that the values reduce the value of the error metric while satisfying an additional condition (i.e., a fidelity constraint). The additional condition may be a unit weights fidelity constraint that requires that a sum of the identified variable parameters associated with the one or more input signals that define the desired output signal equal a sum of parameters used in defining the desired output signal.

The additional condition may also be a dipole geometry constraint. When the desired output signal represents a physiologic signal sensed at a first location that is remote from a signal source and the first location is identified relative to the signal source by a first vector, and at least two of the input signals represent the physiologic signal and represent the physiologic signal as sensed at other locations remote from the signal source and identified relative to the signal source by corresponding vectors, the additional condition requires that a sum of the vectors corresponding to the input signals that represent the physiologic signals, with each vector being weighted by the identified variable parameter associated with the corresponding input signal, equals the first vector.

The additional condition may also require that the low-noise output signal represented by the identified variable parameters has a predetermined relationship with the desired output signal. The condition may be imposed by determining an average property of the desired output signal, determining a corresponding average property of the low-noise output signal represented by the identified variable parameters, and requiring that the average property of the low-noise output signal represented by the determined variable parameters differs from the average property of the desired output signal by less than a predetermined amount.

The desired output signal may be defined as a linear combination of two or more of the input signals, and the desired output signal and the low-noise output signal may represent an ECG signal.

The low-noise output signal may be used to produce a measurement of alternans.

The method may be repeated to produce a set of low-noise output signals. These low-noise output signals may be used as input signals for a procedure that produces a further low-noise output signal that may then be used to produce a measurement of alternans.

In another aspect, the invention features measuring two or more primary input signals that include part or all of a desired signal, defining a desired output signal as a combination of one or more of the primary input signals, measuring one or more secondary input signals that include information about noise content in the desired signal, and combining two or more of the primary signals and one or more of the secondary signals to produce an output signal that approximates the desired output signal and has reduced noise relative to the desired output signal.

In another aspect, the invention features measuring one or more primary input signals that include part or all of a desired signal, defining a desired output signal as a combination of one or more of the primary input signals, measuring two or more secondary input signals that include information about noise content in the desired signal, and combining one or more of the primary signals and two or more of the secondary signals to produce an output signal that approximates the desired output signal and has reduced noise relative to the desired output signal.

In another aspect, the invention features a method of reducing noise in an ECG signal by measuring one or more primary input signals that represent the ECG signal, measuring one or more secondary input signals that represent noise in the ECG signal, and dividing the primary and secondary input signals into sets of segments that each represent a beat of the ECG signal. For each set of segments, a relationship between the noise content of the primary and secondary input signals is defined and the input signals are combined in a way that produces an output signal having low noise content.

In another aspect, the invention features a method of obtaining a reduced noise physiologic signal by measuring one or more input physiologic signals, producing a model that generates an output signal as a combination of the primary input signals, producing a noise metric that represents noise in the output signal produced by the model, adjusting parameters of the model so as to cause the noise metric to satisfy a predetermined condition, and producing the output signal using the model and the adjusted parameters. The method may further include measuring one or more secondary input signals containing information related to noise in the primary input signals and producing the model to generate the output signal as a combination of the primary input signals and the secondary input signals. In addition, one or more fidelity constraints may be defined, and the parameters of the model may be adjusted so that the parameters of the model and the output signal satisfy the fidelity constraints. Also, a relationship between noise content in each of the primary and secondary input signals may be measured and the parameters of the model may be adjusted in view of the measured relationship to reduce or cancel noise from the output signal. Other features and advantages of the invention will become apparent from the following description of the preferred embodiment, and from the claims.

BRIEF DESCRIPTION OF THE DRAWING

FIG. 3 is a placement diagram for electrodes on a patient.

FIG. 4 is a table illustrating the location and type of the electrodes of FIG. 3 and defining the input signals that are recorded from those electrodes.

FIG. 5 is a flowchart of a procedure for producing a low-noise output signal based on information included in multiple input signals.

FIG. 6A is a table of matrix notations.

FIG. 6B is a table of matrix filter notations.

FIG. 7 is a collection of matrices.

FIG. 8 is a flowchart of a procedure for producing an error metric.

FIG. 25 is a table defining coefficients for combining the input signals to create the low-noise output signals.

DESCRIPTION OF THE PREFERRED EMBODIMENTS

Figure 2:
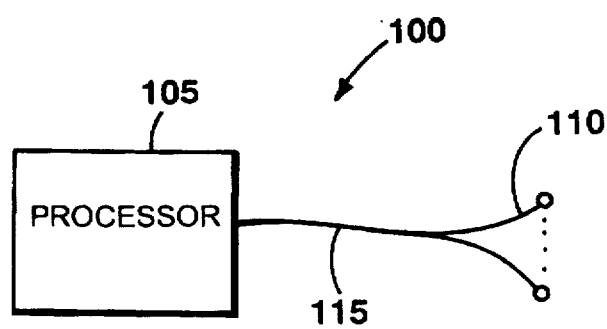
FIG. 2 is a block diagram of an ECG system.

Referring to FIG. 2, an electrocardiogram (ECG) system 100 includes a processor 105 and a set of electrodes 110. The electrodes 100 are attached to a patient's skin and positioned to detect electrical signals produced by the patient's heart. The electrodes include an electrically conductive gel that contacts the patient's skin and conducts to the electrode any electrical signals that are present at the skin. Leads 115 connected between the electrodes 110 and the processor 105 provide the detected signals to the processor 105 for processing and display.

Figure 1:
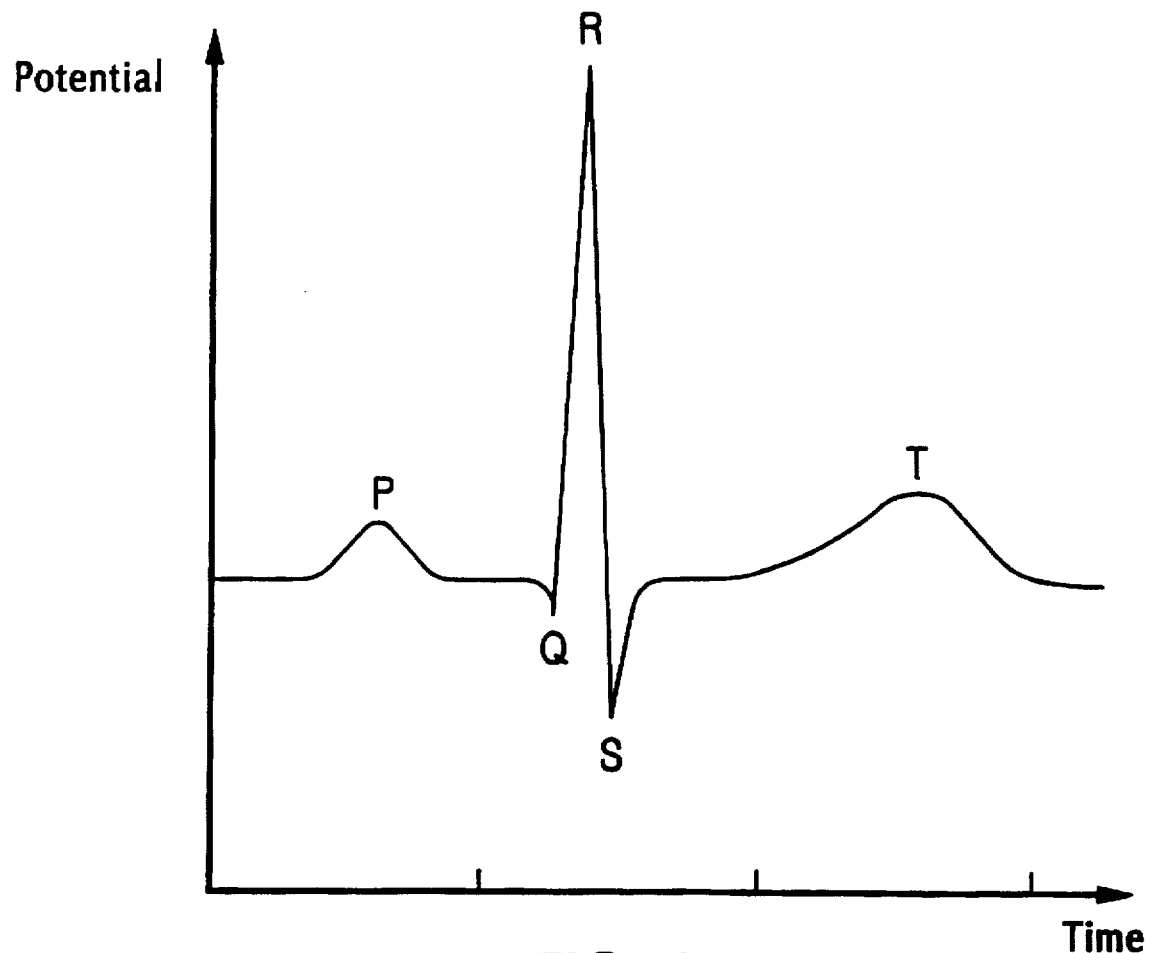
FIG. 1 is an ECG potential over a single beat.

The patient's heart produces an electrical signal that is referred to as an ECG waveform and is illustrated in FIG. 1. Processor 105 analyzes the ECG waveform to detect alternans, a subtle beat-to-beat change in the repeating pattern of the ECG waveform that can be indicative of electrical instability of the heart and increased susceptibility to sudden cardiac death. Alternans results in an ABABAB ... pattern of variation between the shapes of successive beats in the ECG waveform. The level of variation is taken as a characterization of an individual's cardiac electrical stability.

An ECG waveform for a single beat is typically referred to as a PQRST complex. The P wave appears at initiation of the beat and corresponds to activity in the atria, while the QRST complex follows the P wave and corresponds to ventricular activity. The QRS component represents the electrical activation of the ventricles, while the T wave represents the electrical recovery thereof. The ST segment is a relatively quiescent period. In humans, it has been found that the T wave is the best interval of the ECG complex for detecting alternans. That is, a level of variations in the T waves of alternating beats is a good indicator of a patient's cardiac electrical stability.

The ECG signal produced by the patient's heart decreases as a function of the distance from the heart at which it is measured. Accordingly, an ECG signal detected by an electrode 110 will vary from the actual ECG signal based on the placement of the electrode relative to the heart. An accurate approximation of the actual ECG signal may be generated by combining signals from multiple electrodes having known placement relative to the heart.

The ECG signal measured at the body surface may be represented by modelling the heart as a three-dimensional dipole source that produces an electrical signal which varies based on the distance from the heart in the X, Y and Z directions. Thus, the voltage detected by an electrode M that is located relative to the dipole at a coordinate given by the vector $(x_M, y_M, z_M)$ will be:

$$M(t) = x_M v_X(t) + y_M v_Y(t) + z_M v_Z(t).$$

Use of the dipole vector model of the heart has lead to the development of clinical systems that measure the X, Y and Z components of the dipole source through a linear combination of several electrodes. The most common known XYZ systems are the Frank lead system and the Bipolar system. In clinical practice, another common system of electrodes is the twelve lead system. The twelve lead system places greater emphasis on the electrodes on the left chest near the heart.

ECG system 100 includes fourteen electrodes 110 that are placed on the patient as illustrated in FIG. 3. This arrangement combines the electrodes of the Frank and standard 12 lead systems. The signals produced by the electrodes, along with their types, are illustrated in FIG. 4. Seven of the electrodes are conventional ECG electrodes having a single terminal (and producing a single signal), while the other seven electrodes are multi-segment electrodes having four terminals (and producing up to four signals).

The processor 105 acquires the signals produced by each of the electrodes by periodically sampling the signals. When recording an ECG signal, the processor 105 uses an isoelectric point of the signal as a zero voltage reference. The processor 105 measures the isoelectric point during the PQ interval between the P wave and QRS complex. The PQ interval is a good approximation to a zero ECG level because there is no major electrical activity in the heart at that time.

After acquiring the signals, the processor 105 processes the signals to produce an ECG waveform for further analysis or display. While an ECG waveform typically has a QRS amplitude measured in millivolts, an alternans pattern of variation with an amplitude on the order of a microvolt may be clinically significant. Accordingly, the processor 105 must produce the ECG waveform with extreme accuracy to permit effective detection of alternans. Achievement of this accuracy is complicated by the presence of noise in the electrode signals, as the noise may result in beat-to-beat variations in the ECG waveform that have a larger magnitude than the alternans pattern of variation.

The noise in an ECG signal can be classified into three categories: baseline noise generated in the electrode, physiologic noise, and external electrical noise. The baseline noise is low frequency noise that appears as an undulating baseline upon which the ECG rides. Baseline noise is attributable to motion and deformation of an electrode and its associated gel, and results from low frequency events such as patient respiration and patient motion. As a result, the magnitude of baseline noise tends to increase with exercise. However, it is during exercise that many important ECG measurements need to be made. Typically, the frequency content of baseline noise is below 10 Hz.

Physiologic noise results from other physiologic processes within the patient that interfere with the ECG signal, with skeletal muscle activity being the most common source of physiologic noise. The electrical activity of the skeletal muscles creates potentials that are additive with respect to the potentials created by the heart. The frequency content of the skeletal muscle signals is comparable to the frequency content of the QRS complex, and is typically greater than 10 Hz. When measuring T wave alternans, additional physiologic noise may result from changes in the position of the heart due to respiration or from changes in the projection of the electrical potential from the heart to the skin surface due to thoracic conductivity changes arising from the inflation and deflation of the lungs with respiration.

External electrical noise results, for example, from ambient electromagnetic activity in the room, electrode cable motion, and variations in amplifiers or other components of the ECG circuitry. External electrical noise may be eliminated or reduced through the use of high quality components and through the reduction of ambient electromagnetic activity by, for example, deactivating high power equipment.

Noise in the ECG waveform can easily mask the presence of alternans. The noise can also mimic the presence of alternans where there is none. For example, if a patient is breathing at one-half or one-third of the heart rate, the respiration may introduce a harmonic signal having the ABABAB ... pattern of alternans. Similarly, motion that repeats with some periodicity, such as that resulting from exercise, can create electrode noise with a similar pattern. Furthermore, noise resulting from different sources, such as respiration and electrode noise, can interact and produce new periodicities, one of which may mimic alternans.

Noise can also adversely affect the measurement of other ECG parameters, such as the level of the ST segment. Baseline noise can interfere with measurement of the ST level of an ECG signal by misrepresenting the level of the ST segment. Clinically, a change in the ST level of greater than 0.1 millivolts is considered significant. The ST level is typically measured at 80 milliseconds beyond the end of the QRS complex and is measured relative to the isoelectric level determined from the PQ interval. Assuming that the PQ interval is approximately 200 milliseconds away from the ST segment point, a low frequency waveform that is changing at a rate of 0.5 mV per second can misrepresent the ST level by 0.1 mV (0.5 mV/second*0.2 second). Muscle noise can also affect the ST level measurement. Muscle noise appears in bursts coordinated with muscle activity. Muscle noise can easily be on the order of 0.1 mV RMS, hence it can introduce a substantial error into the measurement of the ST level of any single ECG complex.

Similarly, baseline noise can interfere with the T wave alternans measurement because the frequency content of baseline noise often overlaps with the frequency content of T wave alternans. T wave alternans occurs at a frequency of every other beat. Thus, a heart rate of 60 beats per minute corresponds to an alternans repetition rate of 0.5 Hz. Since alternans is typically measured at heart rates between 60–120 beats per minute, the alternans rate is typically between 0.5 and 1 Hz. Baseline noise can have frequency components that occur at a frequency of every other beat, especially when the noise is driven by a periodic phenomenon such as respiration. When baseline noise occurs at a frequency of every other beat, it can mimic alternans. Typically, however, baseline noise is a broadband signal having a power spectrum that contains random levels of noise at different frequencies.

Processor 105 measures the level of alternans ($P_{alt}$) is measured as the energy level of an ECG signal at 0.5 cycles/beat (referred to as $P_{0.5}$) minus the average energy level in a noise reference band between 0.43 and 0.48 cycles/beat (referred to as $P_{noise}$):

$$P_{alt}=P_{0.5}-P_{noise}.$$

Alternans is considered significant when $P_{alt}$ is more than three times the standard deviation of $P_{noise}$. Processor 105 reports the alternans results as $V_{alt}$, which is the square root of $P_{alt}$, and the alternans ratio, which is $P_{alt}$ divided by the standard deviation of $P_{noise}$. When there is a random component at the alternans frequency, the component can create a false alternans measurement.

To effectively detect alternans, processor 105 is configured to reduce the noise in the ECG waveform that it produces. Processor 105 achieves substantial reductions in the noise content of the beats of the ECG waveform by combining one or more ECG signals and one or more other signals in a way that causes the noise content of the signals to combine destructively while preserving the ECG content.

Referring to FIG. 5, the processor 105 achieves noise reduction by implementing a generalized procedure 200. As a first step in the procedure, the processor acquires primary and secondary signals from the electrodes 110 as discussed above (step 205). Primary signals are signals that are directly related to a desired output signal while secondary signals are signals that provide information about the noise content of one or more primary signals. For example, an ECG signal produced by an electrode 110 may be a primary signal while a voltage related to the impedance of an electrode 110 is a secondary signal. It is important to note that the terms "primary" and "secondary" have no functional or mathematical significance, and instead are used solely for ease of description. For example, the impedance signal mentioned above would be a primary signal if the impedance of the electrode was a desired output.

Since ECG waveforms generally consist of linear combinations of signals, much of the generalized procedure lends itself to description using matrix notation, and such notation is used throughout the application. Other embodiments may employ other notations or may employ non-linear signal combinations. For example, the signals could be considered over time instead of over the beats. Summaries of the key matrices and matrix filters employed in the procedure are provided in FIGS. 6A and 6B. Matrix notation for a simplified example is provided in FIG. 7. Matrix notation permits input signals to be linearly combined by matrix multiplication. More general formulations that include non-linear combinations could also be made.

The processor 105 groups the samples of the primary and secondary input signals according to the ECG beat to which they correspond (step 210). For this purpose, a beat matrix $B(n)$ is defined as containing samples of the input signals that are produced during the nth beat. Each row of $B(n)$ corresponds to one signal, and each column corresponds to one point in time in the signal. For example, if there are 32 input signals and measurements are made at 20 locations on each beat, the nth beat is represented by a beat matrix $B(n)$ that has 32 rows and 20 columns. Typically, every entry in a column of $B(n)$ is produced in one time interval so that each column includes the values of all of the input signals for a particular moment in time. As illustrated in FIG. 7, a beat matrix 300 for a system having two primary signals (P1, P2) and one secondary signal (S1) would have three rows and m columns, where m is the number of samples in a beat. The $B(n)$ matrices may be processed prior to their use in the noise-reduction technique. The processing may be general, such as raising the coefficient of the matrices to a power, or may involve more complex processes. The processed matrices may be used to replace part or all of the original matrices, or may be included as additional information.

Next, processor 105 expresses the desired output signal $S(n)$ in terms of the primary signals (step 215). For this purpose, the processor 105 expresses the desired output signal as a linear combination of one or more of the primary signals. The desired output signal can have one or more dimensions.

In the generalized procedure, the matrix F represents the coefficients of the linear combination that defines the desired output signal prior to noise-reduction. The desired output signal $S(n)$ is written as:

$$S(n)=F*B(n),$$

where "*" denotes a matrix multiplication. Each row of F corresponds to an output dimension of $S(n)$. Each column of F corresponds to the signal in a row of $B(n)$. Typically, processor 105 generates the coefficients of F based on information about the placement of the electrodes, and the coefficients of F are usually the same for all beats.

In the simplest case, where the desired output signal is one of the input signals, all entries in the matrix F are zero except for entries in the column corresponding to that one input signal. An output corresponding to a single lead (where a lead is a combination of the signals from two electrodes 110) such as, for example, an X lead that represents the component of the ECG beat in the X direction, is an example of a one dimensional output. In this example, F includes only one row and S(n) is expressed as:

$$S_X(n) = F_X * B(n).$$

An example of a multi-dimensional output is an output corresponding to a trio of leads such as the X, Y and Z leads (which represent the components of the ECG beat in the X, Y and Z direction). In this example, F includes three rows and S(n) is expressed as:

$$S_{XYZ}(n) = F_{XYZ} * B(n).$$

In this case, the row of $F_{XYZ}$ that corresponds to the X lead is the same as $F_X$. Here $F_{XYZ}$ defines the coefficients that constitute the Frank XYZ orthogonal lead system.

In the example illustrated in FIG. 7, the desired output 305 is generated by averaging the two primary signals. Thus, the F matrix 310 includes one row and three columns, with the coefficients of the first two columns (corresponding to P1 and P2) being 0.5 and the coefficient of the third column (corresponding to S1) being 0.

Next, the processor 105 models a low-noise output signal O(n) as a linear combination of one or more primary or secondary signals (step 220). The matrix T represents the coefficients of the linear combination, and the low-noise output signal O(n) is written as:

$$O(n) = T * B(n)$$

In the example illustrated in FIG. 7, the low-noise output 315 is generated by combining the two primary signals and the secondary signal. Thus, the T matrix 320 includes one row and three columns.

Once the model of the low-noise output signal O(n) is defined, the processor 105 considers the error metric E(n) for different values of T (step 225). The error metric is usually a measure of the noise content of the low-noise output signal O(n). Although the error metric can be a general combination of the input signals, it is common to use simple linear or quadratic error measures. An example of an error measure composed of linear and quadratic processing is demonstrated below. The processor generates the error metric by first filtering the low-noise output signal O(n) using a filter $h_1(n)$ that passes frequency bands corresponding to noise and attenuates other frequencies to create an error signal C(n). Thereafter, the processor squares the error signal C(n) to create a noise correlation matrix $R_c(n)$ that the processor then averages with a filter $h_2(n)$ to produce an average noise correlation matrix $R_E(n)$. The noise correlation matrix expresses a relation between the noise in each of the input signals relative to the noise in the other input signals. To the extent that the noise is caused by underlying mechanical or physiologic processes such as movement, respiration or muscle noise, the noise will be related in the various input signals. $R_E(n)$ as described here embodies this relationship in the form of a correlation matrix optionally weighted by the filter $h_2(n)$, which produces a weighted average of the noise correlation matrix for a range of beats. Finally, the processor 105 generates the error metric E(n), which represents the residual noise power remaining after the input signals are combined using the relationship expressed in the average noise correlation matrix $R_E(n)$.

While this procedure is well served with simple linear filters $h_1(n)$ and $h_2(n)$, other approaches may require other, possibly more complicated transformations of the low-noise output signal O(n) to create an error metric E(n).

Figure 9A:
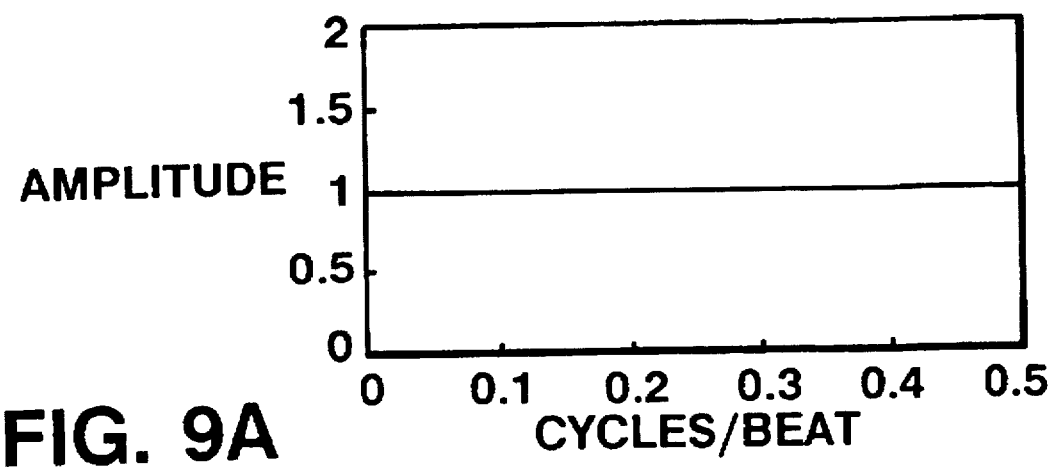
FIGS. 9A-9C are graphs of filter outputs relative to input frequency.
Figure 9B:
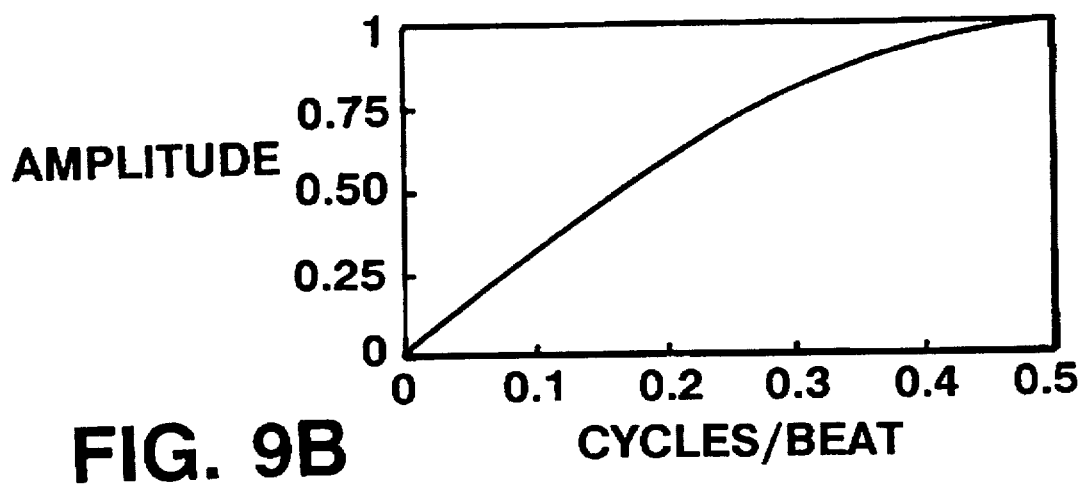

Referring to FIG. 8, the processor 105 creates an error signal C(n) by filtering the low-noise output signal O(n):

$$C(n) = h_1(n) \otimes O(n),$$

where $\otimes$ is the convolution operator (step 350). It should be noted that the filtering here is not over time. Rather, the filtering is over beats and, as a result, operates in a frequency domain that is in cycles per beat. Thus, C(n) for a particular beat n may be based on information for one or more preceding beats (e.g., n−1 or n−2) or one or more following beats (e.g., n+1 or n+2). The filter operates on the same element of a matrix for successive beats (i.e., successive values of n). The role of $h_1(n)$ is to retain within the error signal C(n) the frequencies of O(n) that are to be suppressed as noise. For example, if all frequencies are to be suppressed equally, then $h_1(n)$ may implemented as an all-pass filter that retains all frequencies within the error signal C(n):

$$h_1(n) = \delta(k-n),$$

where $\delta(n)$ is a delta function that equals 1 when k equals n and equals 0 when k has any value other than n. The frequency response of this filter is illustrated in FIG. 9A. To suppress frequencies near the alternans frequency (0.5 cycles/beat) to a greater degree than other frequencies, the filter may be implemented as:

$$h_1(n) = [\delta(k-n) - \delta(k-n-1)]/2,$$

which has the frequency response sin(2 πf), where f is in cycles/beat. The frequency response of this filter is illustrated in FIG. 9B. To suppress frequencies in the band from 0.25 to 0.5 cycles/beat, the filter may be implemented as:

$$h_1(n) = \frac{1}{8}e^{i\pi k/4}, \text{ for } k=n-4 \text{ to } n+3; \ h_1(n)=0, \text{ otherwise.}$$

Figure 9C:
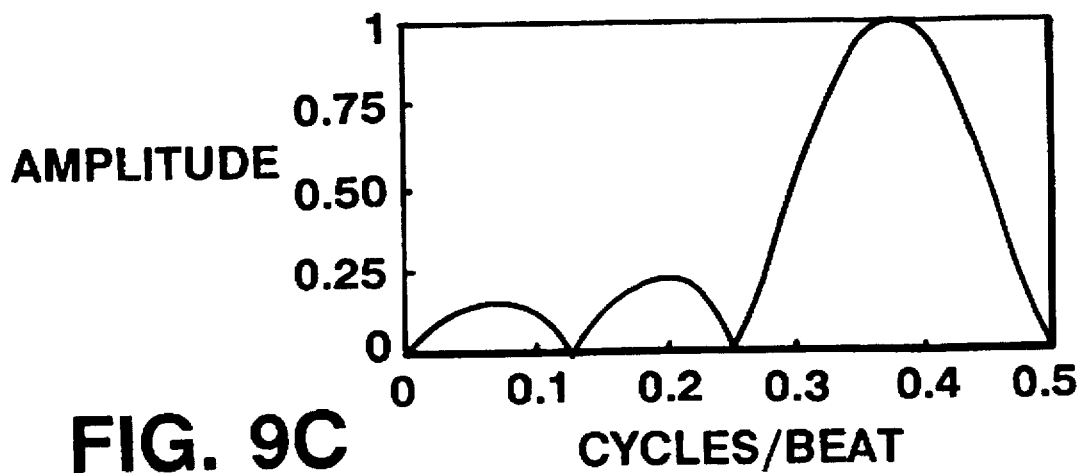

The frequency response of this filter is shown in FIG. 9C. This filter is useful in reducing noise in the band that contains the noise reference for the alternans computation.

The processor 105 then determines the square of the error signal, $R_C(n)$ as:

$$R_C(n) = C(n) * C(n)'.$$

where C(n)' is the transpose of C(n) (step 355). Defining D(n) to be the filtered version of the beat matrix B(n):

$$D(n) = h_1(n) \otimes B(n),$$

and recognizing that $$C(n) = T * D(n),$$

the square of the error signal may be expressed as:

$$R_C(n) = T * R_D(n) * T'$$

where $$R_D(n) = D(n) * D(n)'.$$

The matrix $R_D(n)$ contains the correlation of the noise between all of the input signals, including the primary signals and the secondary signals.

Next (step 360), the processor 105 generates an averaged noise correlation matrix $R_E(n)$ by filtering $R_D(n)$ with $h_2(n)$:

$$R_E(n) = h_2(n) \otimes R_D(n).$$

Typically, $h_2(n)$ is a filter that takes the average value of $R_D(n)$ in a neighborhood around n. The size of the neighborhood is determined by the length of the impulse response of $h_2(n)$. Of course, $h_2(n)$ can also be an all pass filter.

Finally (step 365), the processor generates the error metric for the nth beat, E(n), as:

$$E(n)=tr[T*R_E(n)*T]_1$$

where tr[ ] is the trace operator and provides the sum of the diagonal elements of the given matrix. Since the diagonal contains the correlation of the signal with itself, it contains the power of the signal. Thus, E(n) is a measure of the error signal power in the neighborhood of the nth beat. Recognizing that the correlation matrix $R_E(n)$ expresses the relationship of the noise between all of the input signals, it becomes apparent that the error metric E(n) is minimized when the signals are combined in a way that causes the noise to cancel.

Referring again to FIG. 5, once the error metric E(n) is defined, the processor 105 assigns values to the coefficients of the matrix T used in producing the low-noise output signal O(n) (step 230). In assigning the values, the processor 105 attempts to minimize the error metric while ensuring that the coefficients conform to certain fidelity constraints. The fidelity constraints ensure that the coefficients in the matrix T produce a reasonable low-noise output signal O(n).

Fidelity constraints are of two basic kinds. The first kind, referred to as fidelity to the model constraints, directly constrain the coefficients of T so that the coefficients take on values that embody a priori knowledge about the reasonableness of the model. The second kind, referred to as fidelity to the output signal constraints, constrain the ways that O(n) can differ from S(n). The processor 105 may use either one or both kinds of fidelity constraints in a particular application.

Fidelity to the model constraints for the linear matrix formulation may be expressed as:

$$T*P=Q$$

This relationship can be understood by considering an example in which two identical primary ECG signals contain differing levels of noise and there are no secondary signals. In this example, the low-noise signal is a weighted average of the two signals, and the T matrix includes one row and two columns. To include only one unit of ECG in the low-noise output, the sum of the two coefficients in T must equal one. Accordingly, the parameters P and Q are:

$$P=[1\ 1]'\ \text{and}\ Q=[1].$$

This fidelity constraint is called the "unit weights constraint." The units weight constraint is appropriate for primary signals that are considered to be equivalent.

Figure 10:
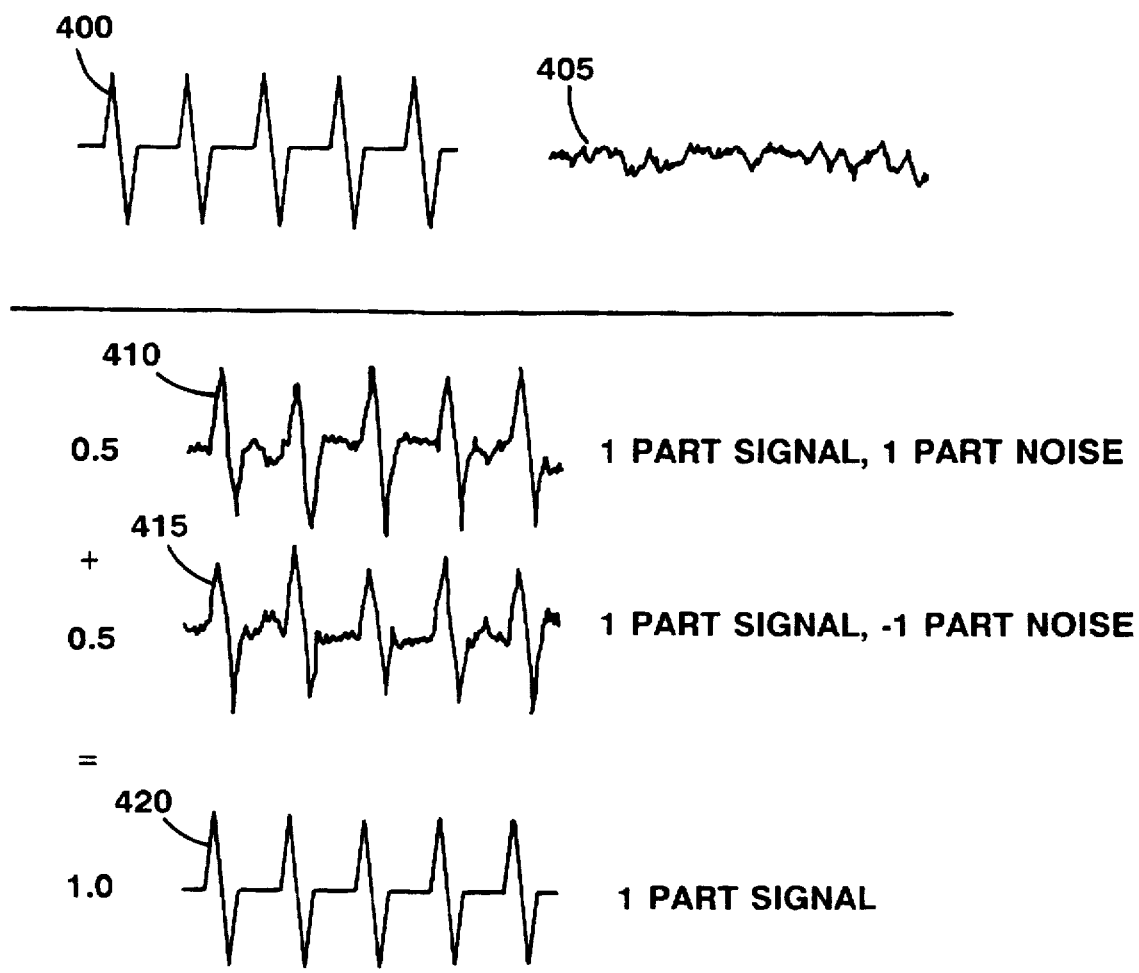
FIG. 10 includes plots of signal waveforms over time.

The unit weights constraint is illustrated by the following example. Referring to FIG. 10., a desired signal 400 and noise 405 are included in different amounts in signals 410 and 415. By taking the proper combination of signals 410 and 415 (i.e., one half of each) a resulting signal 420 is created for which the noise is reduced without distortion of the signal. In this example, the matrix T would be:

$$T=[0.5\ 0.5].$$

With P and Q having the values discussed above, T would satisfy the unit weights constraint:

$$T*P=[0.5\ 0.5]*[1\ 1]'=[1]=Q.$$

The unit weights constraint is applicable to simple systems such as the system illustrated in FIG. 10. In that system, the desired signal appeared with equal amplitude and polarity in both signal 410 and signal 415, while the noise had equal amplitude but opposite polarity in the two signals. This permitted a simple average to yield a perfect reconstruction of the signal.

Figure 11A:
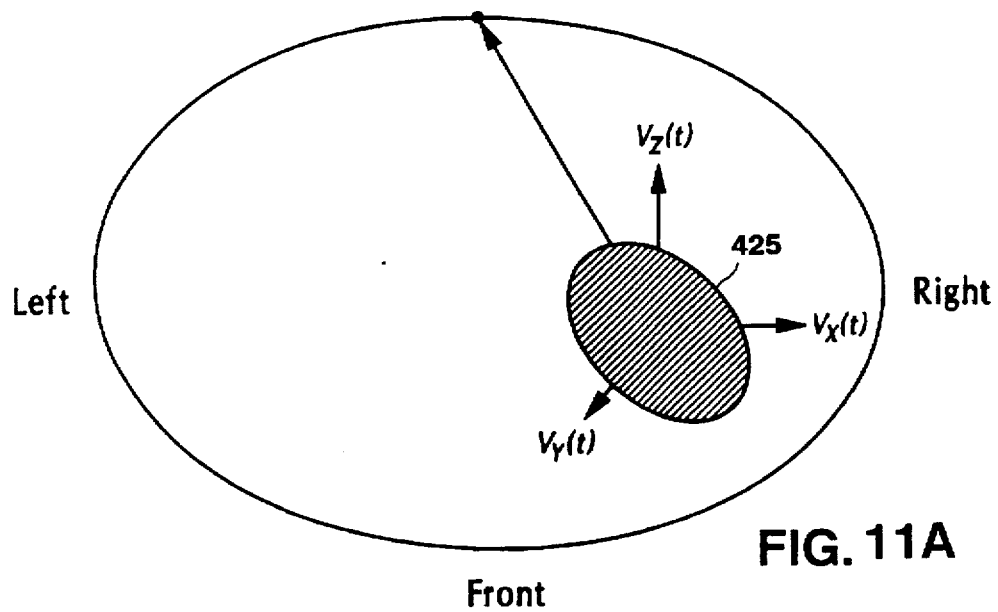
FIG. 11A is a schematic diagram of a heart represented as a dipole source.
Figure 11B:
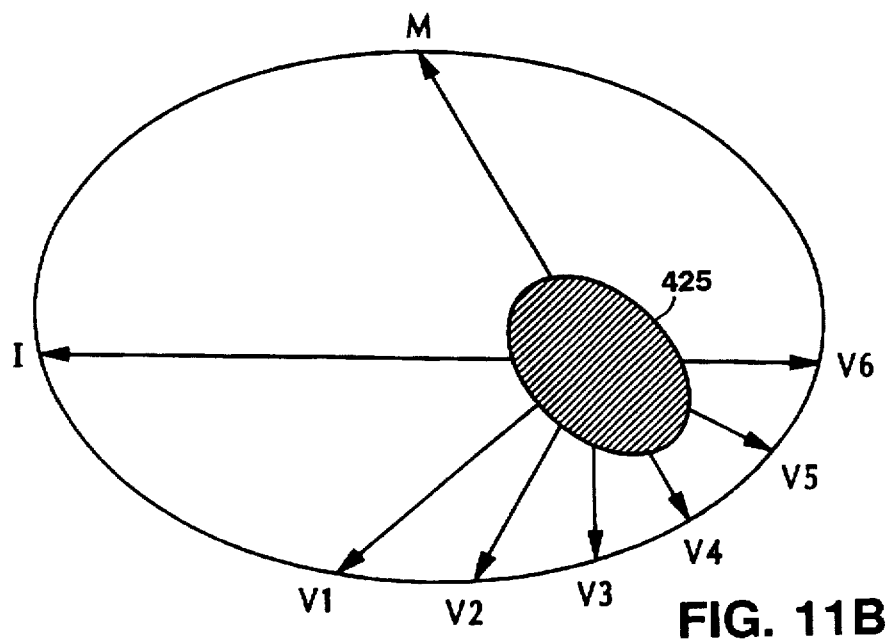
FIG. 11B is a schematic diagram of clinical ECG measurements represented as vector projections of a dipole source.

Referring to FIGS. 11A and 11B, another fidelity to the model constraint is one based on a dipole generator model of the ECG. In FIG. 11A, the heart 425 is depicted at its anatomic position in the chest. As discussed above, the heart is modelled as a three-dimensional dipole source ($v_X(t)$, $v_Y(t)$, $v_Z(t)$) so that the voltage created by the dipole source at an electrode M located at a coordinate given by the vector ($x_M$, $y_M$, $z_M$) relative to the dipole is:

$$M(t)=x_M v_X(t)+y_M v_Y(t)+z_M v_Z(t).$$

The voltage sensed by any electrode placed on the body surface can be viewed as a linear combination of $v_X(t)$, $v_Y(t)$, and $v_Z(t)$. Furthermore, the combination of the voltages from any two or more electrodes can be viewed in terms of the combination of the vector coordinates of those electrodes. For example, by vector arithmetic it is possible to see that some linear combination of the vectors corresponding to the V3 and V5 electrodes should produce a vector that is similar to the vector corresponding to the V4 electrode. By contrast, much of the noise influencing each of the electrodes, such as muscle noise, may have a more local source, and may not be as strongly related between electrodes. Hence, if the signal produced by electrode V4 includes an obscuring noise, a suitable combination of the signals produced by electrodes V3, V4 and V5 might be used to reduce the obscuring noise while preserving the underlying signal present at electrode V4. The generalization of this principle is that each electrode contains some amount of $v_X(t)$, $v_Y(t)$ and $v_Z(t)$, and when taken in the proper combination, a group of electrodes can closely approximate or augment the dipole signal at another electrode while helping to cancel out the noise at that electrode.

When the signals produced by multiple electrodes are combined to produce a signal representative of a single electrode, a fidelity to the model constraint may be applied to the combination. This constraint is based on vector addition and requires that, when the vector corresponding to each electrode is weighted based on the coefficients corresponding to that vector, the sum of the weighted vectors equals the vector corresponding to the position of the single electrode for which the signal is being produced. This constraint is called the "dipole geometry constraint." The unit weights constraint is a special case of the dipole geometry constraint in which all of the input signals are assumed to have equivalent vectors.

The dipole geometry constraint is based on a matrix $P_{XYZ}$ that is defined to be the dipole projection matrix that gives the X, Y and Z coordinates for each input signal relative to the dipole. $P_{XYZ}$ has three columns corresponding to X, Y and Z. Each row of $P_{XYZ}$ corresponds to an input signal. $P_{XYZ}$ can be generated a priori from known positions of the electrodes, or can be computed from specific measurements of the locations of the electrodes on the patient. Although $P_{XYZ}$ can be computed for each beat, it is typically computed only when the underlying conditions of patient heart rate or position change substantially.

One method for generating a useful dipole projection matrix $P_{XYZ}$ is to compute it from a correlation matrix $R_A(n)$ that is the average of one or more correlation matrices $R_B(n)$ given by:

$R_B(n)=B(n)*B(n)'$.

Since B(n) is often noisy, it is usually preferable to filter B(n) by a filter $h_3(n)$ to create an average beat matrix A(n):

$A(n)=h_3(n) \otimes B(n)$ from which a correlation matrix $R_A(n)$ is generated as:

$R_A(n)=A(n)*A(n)'$.

The average beat matrix A(n) is typically generated using a simple low-pass filter that averages a group of 50–150 beats. The dipole projection matrix $P_{XYZ}$ is then generated as:

$P_{XYZ}(n)=R_A(n)*F_{XYZ}'*(F_{XYZ}*R_A(n)*F_{XYZ}')^{-1}$ where $F_{XYZ}$ is the matrix of coefficients for the triplet of points corresponding to the X,Y and Z leads as described above and $(\ )^{-1}$ indicates matrix inversion. The values of P and Q for the dipole geometry constraint are:

$P=P_{XYZ}$ and $Q=F*P_{XYZ}$ so that $T*P=T*P_{XYZ}=F*P_{XYZ}=Q$.

The dipole geometry constraint may be applied in reducing noise from any desired output signal, whether the desired output signal comes from a single vector or is a signal derived from a linear combination of signals recorded at more than one vector coordinate.

It is sometimes desirable to use a priori information about a known ECG dipole having characteristics that it is desirable to preserve in the low-noise output signal if they are present in the input signals. To achieve this, the correlation matrix $R_A(n)$ is combined with the correlation matrix $R_A$ of the known dipole.

The second kind of fidelity constraints, fidelity to the output signal constraints, limit how specific features of the low-noise output O(n) can differ from the equivalent features of S(n). These constraints usually compare only the stable features of S(n) that are least influenced by noise. Typically, the fidelity to the output signal constraints aim to preserve features of the mean of S(n), which can be expressed as:

$\text{mean}[S(n)]=F*A(n)$, where the mean beat matrix A(n) is often the same as produced using filter $h_3(n)$ as discussed above. Similarly, the mean value of the low-noise output signal O(n) may be expressed as:

$\text{mean}[O(n)]=T*A(n)$.

The squared difference of the two mean values is a correlation matrix $R_{MD}(n)$ expressed as:

$R_{MD}(n)=(F-T)*R_A(n)*(F-T)'$.

The total squared error $E_{ET}(n)$ is the sum of the diagonal elements of the correlation matrix, and is expressed as:

$E_{TS}(n)=tr[R_{MD}(n)]=tr[(F-T)*R_A(n)*(F-T)']$, where tr[ ] is the trace operator. This error may be combined with the error metric E(n) to create an aggregate error metric $E_A(n)$:

$\begin{aligned} E_A(n) &= E(n) + \alpha E_{TS}(n) \\ &= (tr[T * R_e(n) * T + \alpha(F-T) * R_A(n) * (F-T)'] \end{aligned}$ The value of T that minimizes $E_A(n)$ is given by:

$T=Q*T_0+\alpha F*R_A(n)*R_0*(I-P*T_0)$ where I is the identity matrix, $R_0=(R_e(n)+\alpha R_A(n))^{-1}$ and $T_0=(P'*R_0*P)^{-1}(P'*R_0)$.

When the error is added to the error metric, it is referred to as a "morphology cost", since the squared morphology error is traded off against the power of the error signal.

The matrix $R_A(n)$ embodies the relationship between the desired output signal components of the input signals. As such, it carries information on how signals may be combined and substituted in a way which preserves the desired signal while the combination is acting to reduce the noise by combining signals in a way that causes the noise to cancel.

The fidelity to the output signal can also be considered as a separate constraint. For example, the squared error of the mean of the low-noise output signal relative to the average desired output signal can be constrained so as not to exceed the total power in the average desired output signal by more than a certain percentage. The percentage may be expressed as:

$Err=100tr[(F-T)R_A(n)(F-T)']/tr[FR_A(n)F']$, where the total power is given by the quantity $tr[FR_A(n)F']$. This constraint is referred to as the "morphology constraint." The solution for T with a morphology constraint is found using the smallest non-negative value $\alpha$ that satisfies the equation for producing a matrix T that minimizes $E_A(n)$ while preventing Err from exceeding 0.9 to 1.1%.

The determination of T is based on some neighborhood of input signals and is applied to produce the low-noise output in another neighborhood. In an adaptive processing implementation, the input neighborhood is some relatively small number of past and future beats. For example, the matrix T may be derived using 16 past beats, the current beat, and 15 future beats. The derived matrix T is then applied to an even smaller number of beats, and is typically applied only to the current beat.

In a batch processing implementation, the input and output neighborhoods are similar, if not the same. The filter $h_2(n)$ may be a simple "boxcar" filter that takes the average over the entire group of beats. The resulting matrix T is then applied to the entire group of beats.

Figure 12:
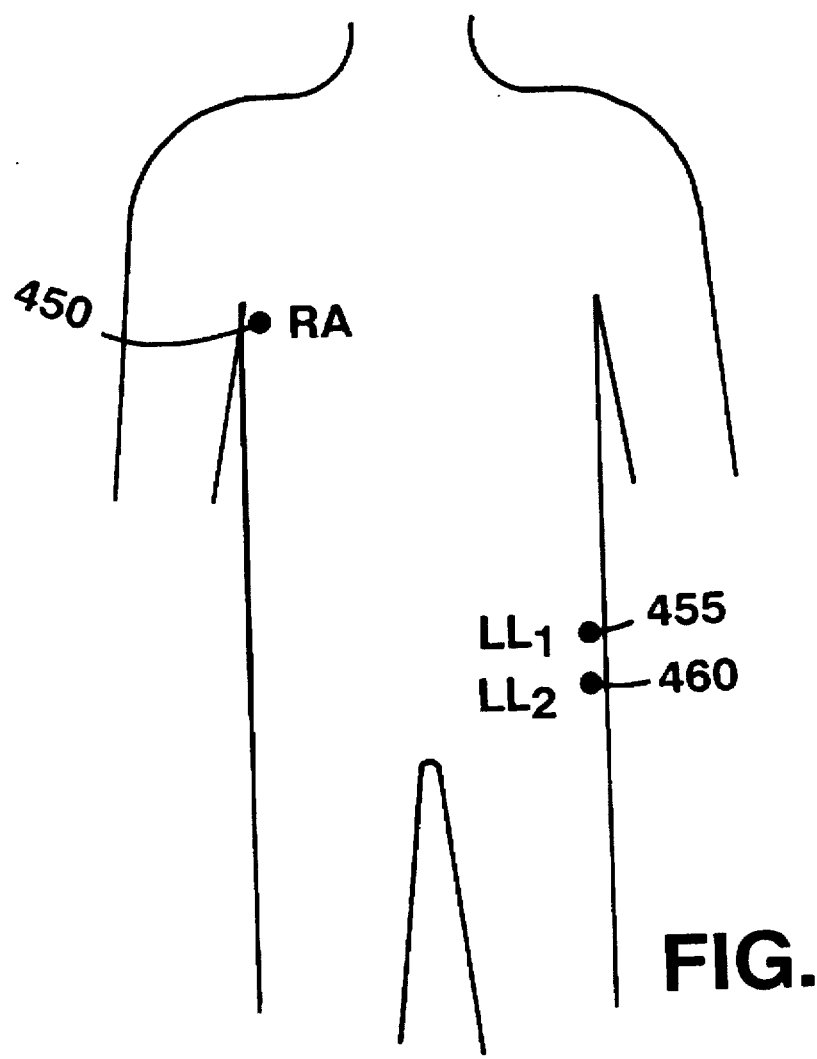
FIG. 12 is an electrode placement diagram for a system having three electrodes.

Referring to FIG. 12, in a simple case, the processor 105 reduces noise a primary signal produced by a pair of primary electrodes 450 and 455 (RA and $LL_1$) using a secondary signal produced by a secondary electrode 460 ($LL_2$). Similar results could also be obtained using only two electrodes. The three electrodes are a subset of the electrodes 110 illustrated in FIG. 3. The first electrode 450 (RA) is positioned just below the patient's right arm. The second electrode 455 ($LL_1$) is positioned on the patient's left side near the patient's left leg. The electrodes 450 and 455 constitute an ECG lead (LL) with the signal produced by the lead being a voltage difference between the leads that is defined as:

$LL=RA-LL_1$

The third electrode 460 (LL$_2$) is positioned next to the second electrode 455 and provides a secondary signal that is related to the impedance (Z$_{LL1}$) of the second electrode 455. The third electrode 460 may be implemented as a separate electrode, or may be implemented as a segment of a multi-segment electrode that includes the second electrode 455. The processor 105 uses the impedance of the second electrode 455 to remove the effects of baseline noise from LL to produce a noise-free lead LL'.

Figure 13:
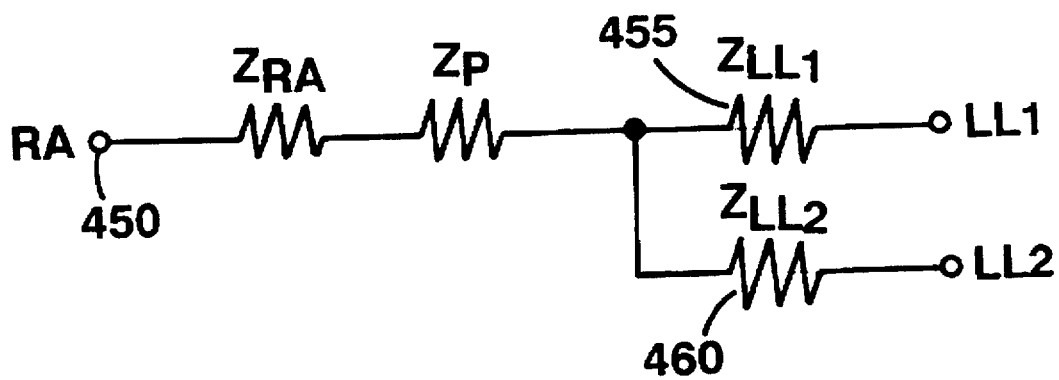
FIG. 13 is a circuit diagram showing the equivalent circuit for the system of FIG. 12.

An equivalent circuit for the system of FIG. 12 is illustrated in FIG. 13. The circuit includes impedances (Z$_{RA}$, Z$_{LL1}$, Z$_{LL2}$) associated with each of the electrodes 450, 455, 460. The impedance Z$_{RA}$ of the first electrode 450 (RA) is arranged in a series configuration with the impedances Z$_{LL1}$ and Z$_{LL2}$ of the second electrode 455 (LL$_1$) and the third electrode 460 (LL$_2$), which are arranged in a parallel configuration relative to each other. The circuit includes an additional impedance Z$_P$ that represents the impedance of the patient. The impedance Z$_P$ is arranged in a series configuration relative to the impedances of the electrodes.

Figure 14:
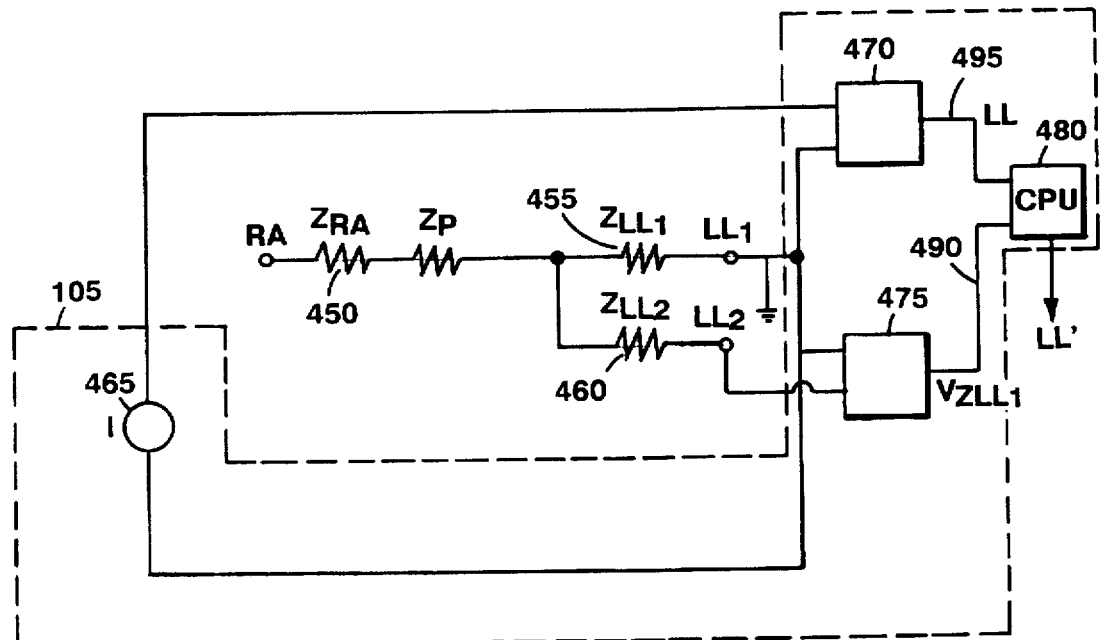
FIG. 14 is a circuit diagram of a circuit for measuring a voltage and an impedance of the system of FIG. 12.

Referring to FIG. 14, processor 105 includes circuitry for measuring LL and Z$_{LL1}$. The circuitry includes a current source 465 that is configured and connected to inject a 56 kHz current between the first electrode 450 (RA) and the second electrode 455 (LL$_1$). The current from the current source 465 flows through the electrode-skin interface of the first electrode 450 (modeled by Z$_{RA}$), through the patient (modeled by Z$_P$) and through the electrode-skin interface of the second electrode 455 (modeled by Z$_{LL1}$). The measurement circuitry and the hardware configuration for this example is similar to the configuration provided by Devlin et al.

The ECG signal ($_{LL}$) is detected by an ECG amplifier 470 that is connected between the first electrode 450 and the second electrode 455. The amplifier 470 includes a low-pass filter that blocks the 56 kHz signal and prevents the signal from affecting LL.

A voltage (V$_{ZLL1}$) corresponding to the impedance (Z$_{LL1}$) of the second electrode 455 is produced by a demodulating amplifier 475 that is connected between the second electrode 455 and the third electrode 460 and is tuned to measure only the portion of the voltage between the second and third electrodes that has a frequency of 56 kHz. The demodulating amplifier 475 has a high input impedance so that current flow into the demodulating amplifier is negligible. Accordingly, there is no 56 kHz voltage drop across the third electrode 460 (LL$_2$) and the voltage (V$_{ZLL}$) measured by the demodulating amplifier 475 corresponds to the 56 kHz voltage drop across the second electrode 455 (LL$_1$). Since the current source 465 provides a constant level of current, Ohm's law dictates that the voltage measured by the demodulating amplifier 475 (V$_{ZLL1}$) is proportional to the impedance (Z$_{LL1}$) of the second electrode 455 as:

$$Z_{LL1} = V_{ZLL1}/I,$$

where I is the current produced by the current source 465. The output of the ECG amplifier 470 (LL) and the output of the demodulating amplifier 475 (V$_{ZLL1}$) are provided to a central processing unit 480 of the processor 105.

Figure 15:
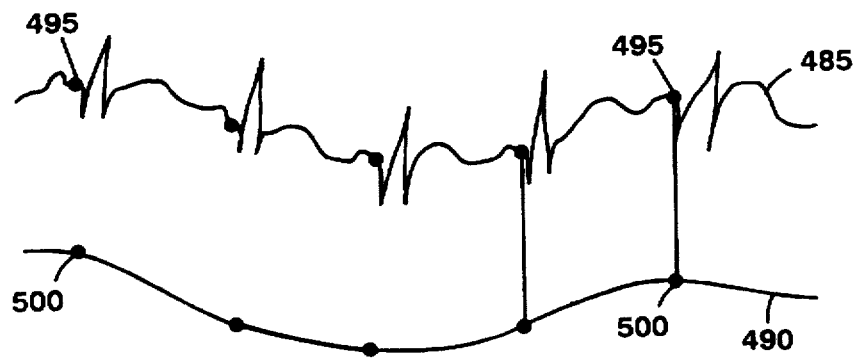
FIG. 15 is a diagram of signals produced by the circuit of FIG. 14.

Referring to FIG. 15, a signal 485 produced by the ECG amplifier 470 includes a series of ECG beats (see FIG. 1) modulated with a low frequency noise signal. A signal 490 produced by the demodulating amplifier 475 includes a low frequency noise signal. The isoelectric points 495 of beats of the signal 485 vary similarly to corresponding points 500 in the signal 490.

The processor 105 modifies the output (LL) of the ECG amplifier 470 based on the output (V$_{ZLL1}$) of the demodulating amplifier 475 according to the procedure 200 discussed above and illustrated in FIG. 5 to produce a low-noise output signal O(n) ($_{LL}$). After acquiring the input signals (step 205), the processor 105 defines a beat matrix B(n) that includes two rows and twenty columns, with the first row corresponding to the output of the ECG amplifier 470 and the second row corresponding to the output of the demodulating amplifier 475 (step 210).

Next, the processor 105 expresses the desired output signal S(n) in terms of the primary signals (step 215). In the described example, the input signals includes a primary signal (LL) that is directly related to the desired output signal and a secondary signal (V$_{ZLL1}$) that provides information about the noise content of the primary signal. In particular, the primary signal (LL) includes the true physiologic ECG signal arising from the heart and baseline noise due to the electrodes and other noise sources, while the secondary signal (V$_{ZLL1}$) includes information about the baseline noise. Accordingly, the processor 105 defines the F matrix as:

$$F=[1\ 0],$$

which indicates that the desired output signal S(n) equals the primary input signal LL.

Next, the processor 105 expresses the low-noise output signal O(n) (or LL') in terms of the primary and secondary signals (step 220). As noted above, the signal 485 (LL) includes the ECG signal plus noise, while the signal 490 (V$_{ZLL1}$) is related to noise. Thus, the low-noise output signal can be expressed as:

$$LL' = LL - con * V_{ZLL},$$

where con is a constant. In matrix notation, this relationship is expressed as:

$$LL' = O(n) = T(n) * B(n)$$

where $$T(n) = [1\ -con(n)],$$

n is a particular beat, and con(n) is a constant applicable to that beat. Thus, the impedance signal is used in a direct linear combinations with the ECG signal. The impedance signal could be used in other ways. For example, if the impedance were related to baseline noise through a non-linear relationship, that relationship could be employed in modifying the ECG signal. A simple example would be to use both the impedance and the square of the impedance in approximating the baseline noise. In addition, impedance signals measured at different or multiple frequencies could also be used.

Next, the processor 105 defines an error metric for the nth beat (step 225) as the squared deviation of the isoelectric point of O(n) from the neighborhood average in a neighborhood of eight beats. Processor 105 defines the isoelectric point ISO(n) of O(n) from the samples of O(n) in the PQ interval of the beat (see FIG. 1). Processor 105 defines the neighborhood average A(n) for the isoelectric point ISO(n) as:

$$A(n) = \frac{1}{8} \sum_{k=n-7}^{n} ISO(k)$$

where the neighborhood includes the beat being considered and seven immediately preceding beats. The error metric E(n) is then defined as:

where the neighborhood is the same as that for A(n).

$$E(n) = \sum_{k=n-7}^{n} (ISO(k) - A(k))^2$$

Finally, the processor 105 reduces noise in the low-noise output signal O(n) by selecting values for con(n) that minimize the error metric (step 230). (Because the ECG signal appears only in the primary signal, the use of "1" as the first entry of the T matrix inherently satisfies the unit weights fidelity constraint.) The value of con(n) that minimizes the error metric E(n) is:

$$con(n) = \sum_{k=n-7}^{n} ISO(k)V_{ZLL1}(k) / \sum_{k=n-7}^{n} V_{ZLL1}(k)^2$$

The processor 105 uses con(n) as the constant for the isoelectric point for the nth beat. For all other points in the beat, the processor 105 linearly interpolates between the value of con(n) for the nth beat and the value of con(n) for the adjacent beat (i.e., con(n−1) or con(n+1)). For example, a point that is halfway between the isoelectric point of beat n and the isoelectric point of beat n−1 will have a value for con(n) that equals the average of con(n) and con(n−1).

Through use of the impedance signal, the processor 105 produces a low-noise output signal LL' that has substantially reduced noise content relative to the desired output signal LL. However, it has been found that impedance variations for an electrode do not perfectly match the baseline noise for the electrode. It also has been found that multiple impedance signals may be used to further improve the quality of the low-noise output signal. For example, the arrangement illustrated in FIG. 16 provides three impedance signals for use in noise reduction.

Figure 16:
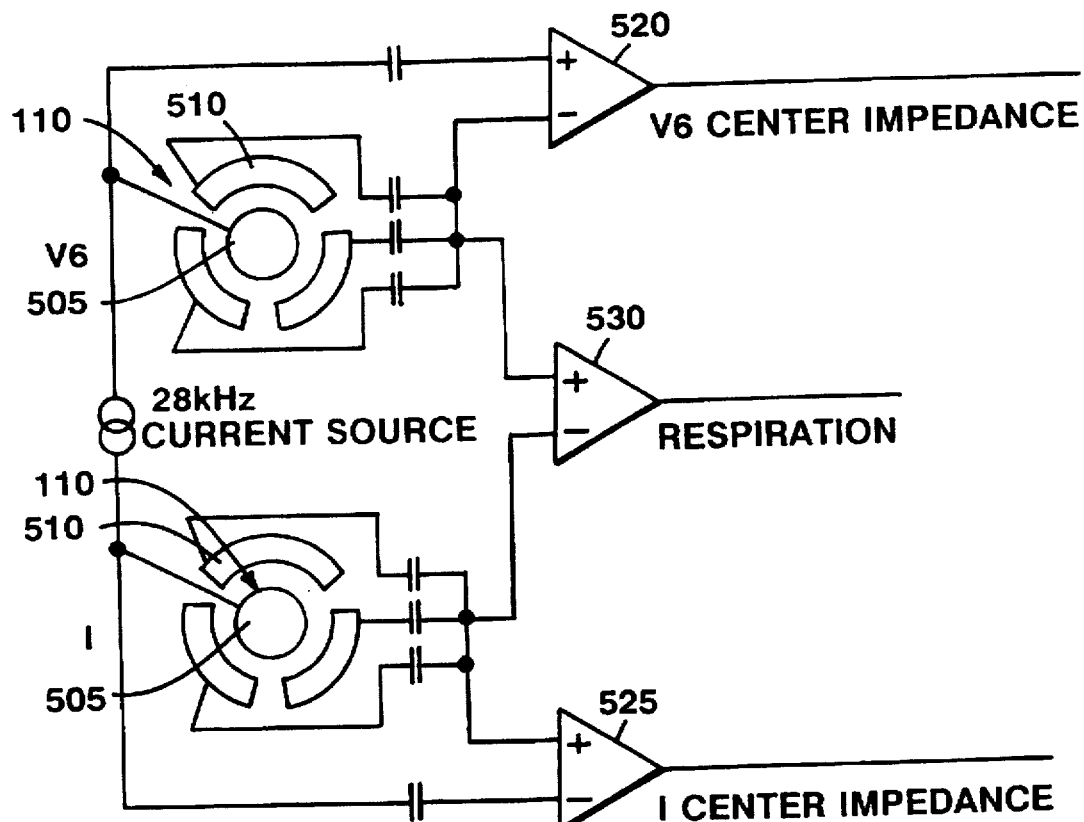
FIG. 16 is a circuit diagram of a circuit for measuring impedances.

FIG. 16 illustrates two electrodes 110 that, as shown in FIGS. 3 and 4, are multi-segment electrodes positioned on opposite sides of the patient's thoracic cavity. Each multi-segment electrode includes a center electrode 505 and a trio of annular segments 510 that are capacitively coupled to function as a ring electrode for purposes of impedance measurement. Similar results could be obtained by replacing each multi-segment electrode with a pair of traditional electrodes.

To produce the impedance signals, a 28 kHz current source 515 is connected between the center electrodes 505 of the two electrodes to inject a current as discussed above. The center electrode 505 and the annular electrodes 510 of the first electrode 110 (V6) are capacitively coupled to the input terminals of a demodulating amplifier 520 that produces an output signal related to the impedance of the center electrode of the first electrode. Similarly, the center electrode 505 and the annular electrodes 510 of the second electrode 110 (I) are capacitively coupled to the input terminals of a demodulating amplifier 525 that produces an output signal related to the impedance of the center electrode of the second electrode.

The annular electrodes 510 of each electrode 110 are connected to a corresponding input terminal of an amplifier 530 that produces a signal that corresponds to the patient's trans-thoracic impedance. The trans-thoracic impedance varies as the patient's lungs inflate and deflate. Thus, the trans-thoracic impedance is indicative of respiration by the patient, which, as previously discussed, is a significant source of baseline noise.

Figure 17:
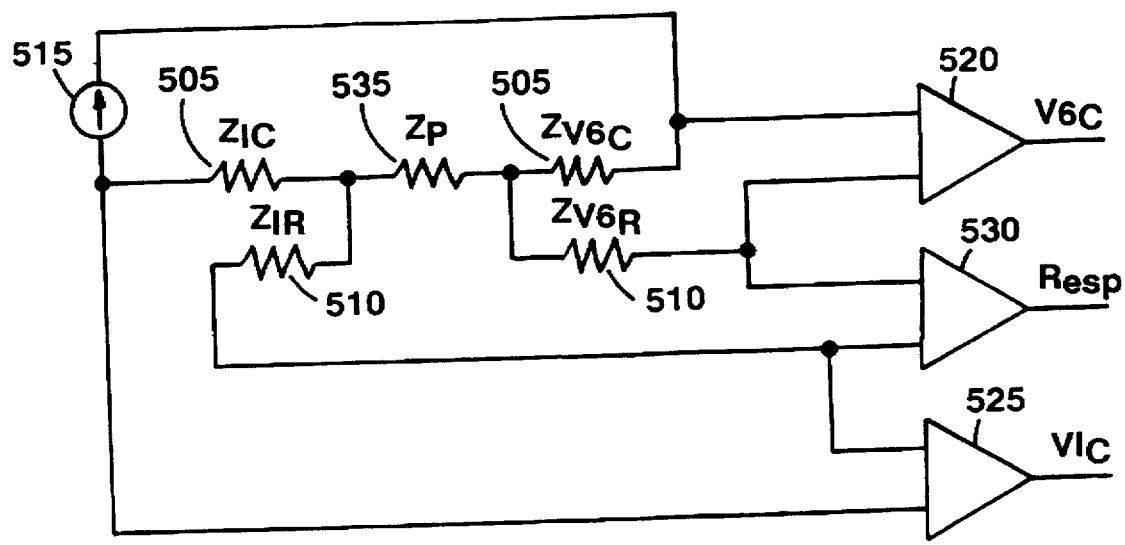
FIG. 17 is a circuit diagram showing an equivalent circuit for the system of FIG. 16.

FIG. 17 illustrates an equivalent circuit for the arrangement of FIG. 16. The circuit includes impedances ($Z_{V6C}$, $Z_{IC}$) associated with each of the center electrodes 505 and impedances ($Z_{V6C}$, $Z_{IC}$) associated with each of the ring electrodes 510. The impedance of each center electrode 505 is arranged in parallel with the impedance of the corresponding ring electrode 510. The parallel impedance arrangement for each electrode 110 is arranged in series with the impedance for the other electrode 110. An additional impedance 535 ($Z_P$) corresponding to the transthoracic impedance is arranged in series between the impedances of the two electrodes 110. The input terminals of the demodulating amplifiers draw essentially no current. For this reason, no current flows through either of the ring electrodes 510. Thus, the voltage difference between the input terminals of demodulating amplifier 520 corresponds to the voltage drop across the center electrode 505 of the first electrode (V6), which corresponds to the impedance ($Z_{V6C}$) of that electrode. Similarly, the voltage differences between the input terminals of the demodulating amplifiers 525 and 530 correspond, respectively, to the impedance ($Z_{IC}$) of the center electrode 505 of the second electrode and the impedance 535 ($Z_P$) of the patient's trans-thoracic cavity.

Figure 18B:
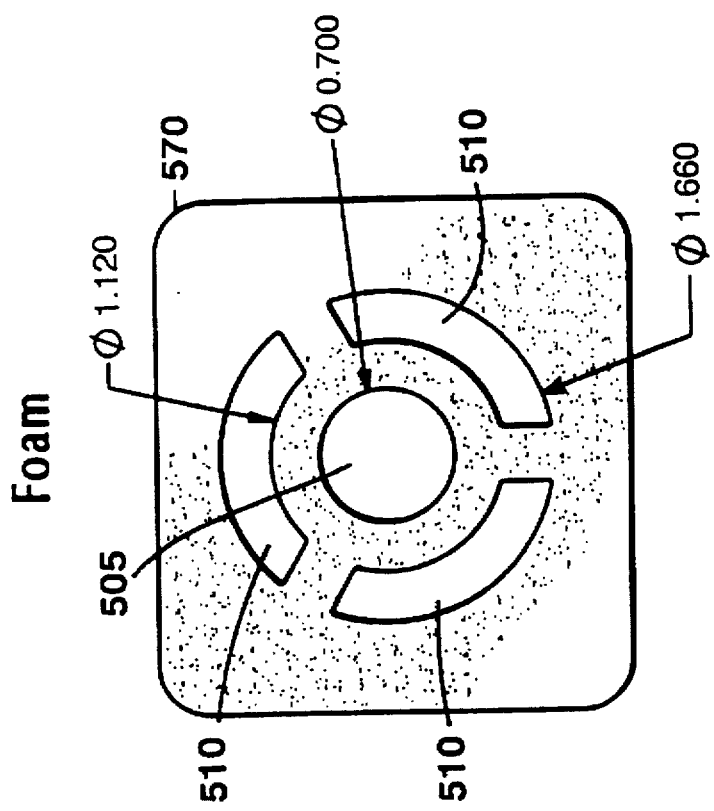
FIGS. 18A and 18B are diagrammatic views of components of a multi-segment electrode.
Figure 18A:
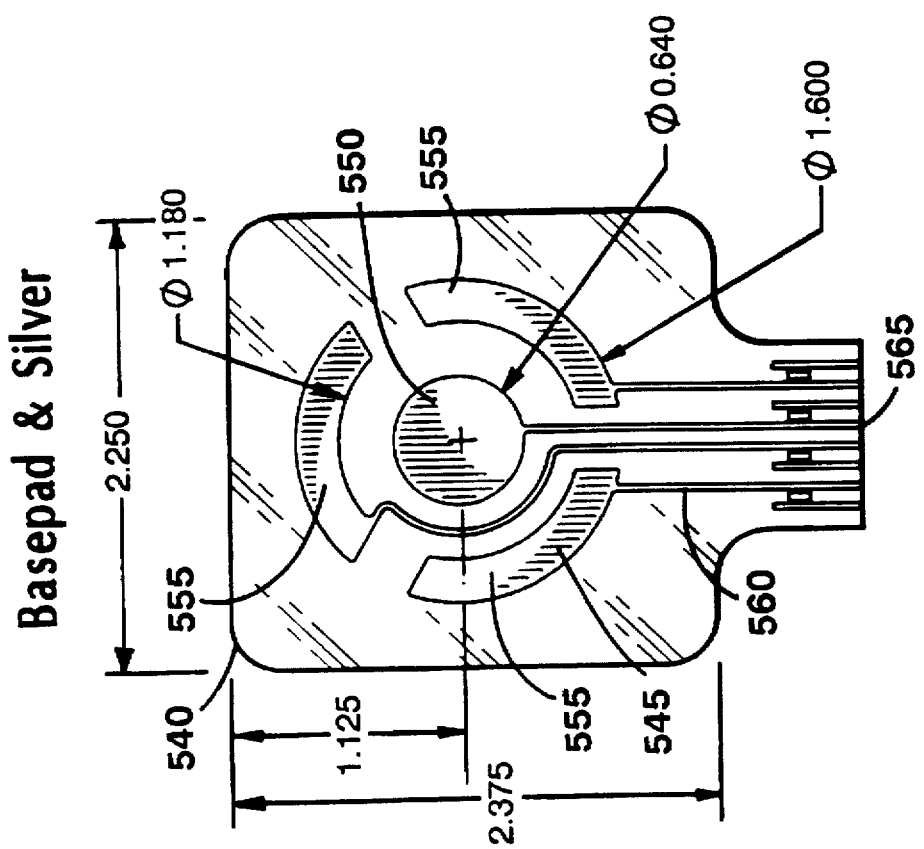

Referring to FIGS. 18A and 18B, multi-segment electrodes are constructed from a film basepad 540 on which is printed silver-chloride ink 545. The ink is patterned to create a center segment 550 and annular segments 555 that provide electrical connection to the electrode gel. The ink pattern also creates traces 560 that continue to the bottom edge 565 of the basepad 540. At the bottom edge of the basepad 540, the traces are brought into a parallel configuration suitable for an edge connector.

A plastic flexible foam 570 is attached to the base pad 540. The foam includes cutout sections that correspond to the electrode segments 505, 510 and create wells that hold electrically conductive gel that makes an electrical connection from the ink to the skin. The surface of the foam is covered with an adhesive that adheres the electrode to the skin of the patient. The foam covers and insulates portions of the traces 560.

Figure 19:
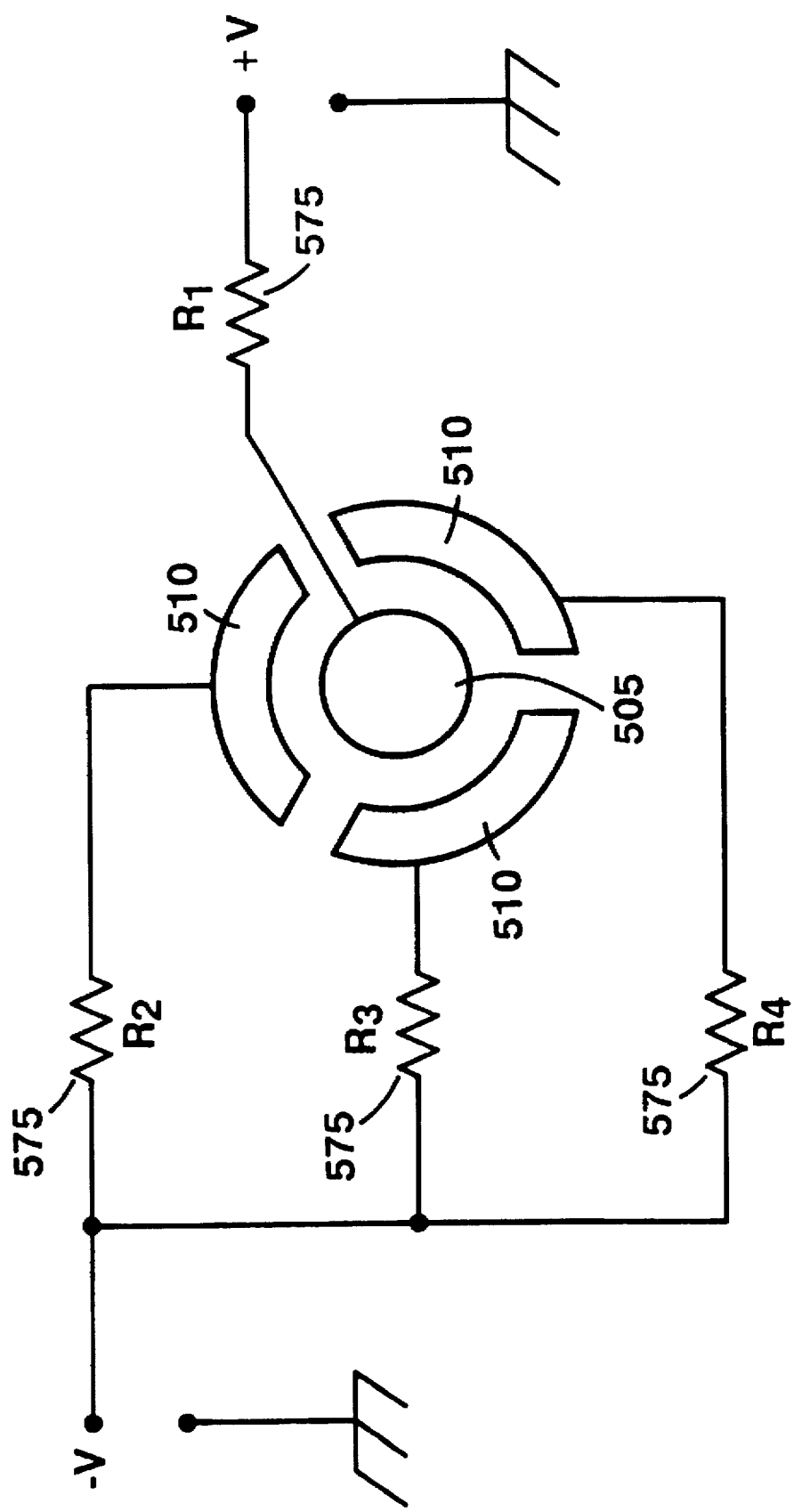
FIG. 19 is a schematic diagram of a circuit for measuring noise created by movement of a multi-segment electrode.

Multi-segment electrodes provide a number of advantages. First, an ECG signal typically varies differently (if at all) between segments of the electrode than does baseline noise. This is largely attributable to differences between the physical location of the heart and the locations of sources of noise. It is also attributable to the fact that the segments are all part of the same physical structure and are therefore affected similarly by movement due to respiration or other causes. In addition, variations in noise due to patient movement can be adjusted between segments by introducing different DC bias currents at the each segment of the electrode. Such a biasing system is illustrated in FIG. 19, where the bias current injected at each segment is related to the value of a resistor 575 connected to that segment. Similar results could be obtained by using different electrolyte mixtures in the gel of each segment to vary the conductivity from segment to segment or by using different metal combinations on the foam basepad.

Processor 105 also uses the generalized procedure 105 to implement a technique referred to as "electrode noise reduction." In performing electrode noise reduction, the processor 105 uses multiple equivalent ECG signals and multiple impedances to reduce noise in an ECG signal produced by a lead.

Figure 20:
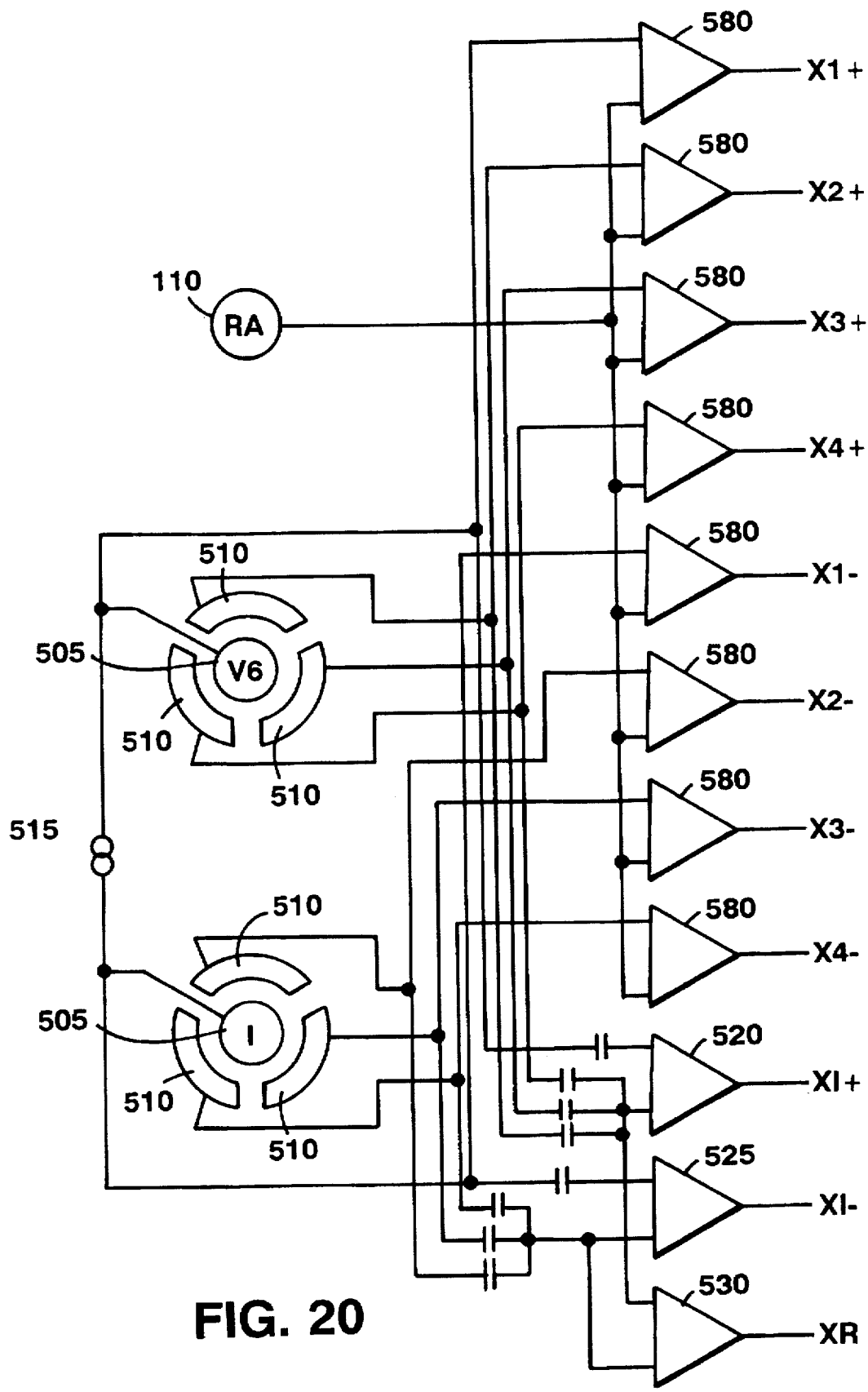
FIG. 20 is a circuit diagram of a circuit used in generating a low-noise signal.

Referring to FIGS. 5 and 20, processor 105 uses the generalized procedure 200 to produce a low-noise output signal ($X_O$) that has substantially reduced baseline noise and is used in the measurement of alternans. Processor 105 produces the low-noise output signal based on eleven signals obtained from electrodes V6, I and RA (see FIG. 3). Eight of the signals (X1+, X2+, X3+, X4+, X1−, X2−, X3−, X4−)

correspond to ECG signals sensed by the segments of the electrodes V6 and I relative to the signal sensed by the electrode RA, and are produced by amplifiers 580. Each amplifier 580 has one input terminal that is directly connected to a segment of one of the electrodes V6 and I and another input terminal that is directly connected to the electrode RA. The electrodes are not capacitively coupled to the input terminals of the amplifiers 580. The remaining signals correspond to the center electrode impedances (XZ+, XI−) and the trans-thoracic impedance (XR) that are produced by the circuit illustrated in FIGS. 16 and 17 and discussed above.

Processor 105 stores two measurements for each beat (step 205). The first measurement corresponds to the isoelectric point and equals the average value of each signal during the PQ interval of the beat. The second measurement is taken 60 milliseconds after the end of the QRS complex of the beat and is referred to as the J+60 millisecond point of the ST segment (the J point is the end of the QRS complex).

Using these measurements, processor 105 generates a beat matrix B(n) having two columns and eleven rows (step 210). Each of the eleven rows of the beat matrix B(n) corresponds to one of the eleven signals, with the signals arranged in the following order: X1+, X2+, X3+, X4+, X1−, X2−, X3−, X4−, XI+, XI−, XR. The coefficients of the first column of the beat matrix B(n) correspond to signal values at the isoelectric point, and the coefficients of the second column correspond to signal values at the J+60 millisecond point.

Next, processor 105 defines the desired output signal (X) in terms of the primary signals (step 215):

$$X = X1+ - X1-.$$

In matrix notation, this is expressed as:

$$X = S(n) = F_X * B(n)$$

where $$F_X = [1\ 0\ 0\ 0\ -1\ 0\ 0\ 0\ 0\ 0\ 0].$$

Processor 105 then defines the low-noise output signal ($X_0(n)$) in terms of primary and secondary signals (step 220):

$$X_0(n) = O(n) = T_X * B(n)$$

where the matrix $T_X$ has one row and eleven columns.

The processor 105 then generates an error metric (step 225). To ensure that the low-noise output signal includes one unit of the X+ (V6) electrode and one unit of the X− (I) electrode, processor 105 imposes the unit weight fidelity constraint as:

$$P = \begin{bmatrix} 0\ 0\ 0\ 0\ 1\ 1\ 1\ 1\ 0\ 0\ 0 \\ 1\ 1\ 1\ 1\ 0\ 0\ 0\ 0\ 0\ 0\ 0 \end{bmatrix}^t \quad Q = [1\ 1]$$

Because the low-noise output signal $X_0$ is to be used in the detection of alternans, processor 105 seeks to minimize the non-alternans signal content of the error signal C(n). For this reason, processor 105 selects the filter $h_1(n)$ to have the transfer function illustrated in FIG. 9B:

$$h_1(n) = [\delta(k-n) - \delta(k-n-1)]/2.$$

Application of this filter results in:

$$C(n) = T_X * D(n)$$

where $$D(n) = B(n) - B(n-1),$$
$$C(n) = h_1(n) \otimes O(n),$$

and $$O(n) = T_X * B(n).$$

Processor 105 then computes the error metric as the square of the error signal over a neighborhood of 32 beats centered around the nth beat. Processor does this by defining $h_2(n)$ as:

$$h_2(n) = 1/32 \text{ for } k = [n-16 \text{ to } n+15]$$
$$= 0, \text{ otherwise}.$$

From this, processor 105 defines $R_E(n)$ as:

$$R_E(n) = h_2(n) \otimes (D(n) * D(n)')$$

or $$R_E(n) = \frac{1}{32} \sum_{k=n-16}^{n+15} (B(k) - B(k-1)) * (B(k) - B(k-1))'$$

As discussed above, the error metric E(n) equals:

$$E(n) = T * R_E(n) * T'.$$

Finally, processor 105 selects coefficients for $T_X(n)$ that minimize the error metric and satisfy the unit weights fidelity constraint (step 230):

$$T_X(n) = Q * T_0,$$

where $$T_0 = ('*R_0*P)^{-1}*(P'*R_0)$$

and $$R_0 = [R_E(n)]^{-1}.$$

Processor 105 generates $T_X(n)$ for each beat, and uses this value to generate a low-noise output signal ($X_0(n)$) according to:

$$X_0(n) = T_X(n) * B(n),$$

where $X_0(n)$ has one row and two columns for each beat, with the first column corresponding to the isoelectric point and the second column corresponding to the J+60 millisecond point.

Processor 105 also uses the matrix $T_X(n)$ to modify all samples in the QRST complex of the beat. For this purpose, processor 105 produces an extended beat matrix $B_{QRST}(n)$ that has eleven rows and a number of columns that equals the number of samples in the QRST complex of the beat. Processor then produces an extended low-noise output signal $X_{QRST}(n)$ as:

$$X_{QRST}(n) = T_X(n) * B_{QRST}(n).$$

In yet another variation, processor 105 imposes a morphology constraint on the low-noise output signal. As discussed above, the morphology constraint is a fidelity to the output signal constraint that forces the average low-noise output signal to conform to the desired output signal. To implement the morphology constraint, processor 105 generates $R_A(n)$ using a filter $h_3(n)$ that averages 100 normal beats over the QRST complexes of the beats. Processor 105 recomputes the $R_A(n)$ matrix for each new beat. However, processor 105 could obtain similar results by recomputing the matrix only when the patient undergoes a significant change in position or heart rate (conditions under which the average beat would be expected to change). With the morphology constraint, the solution for $T_X(n)$ becomes:

$$T_X(n) = Q^*T_0 + \alpha F^* R_A(n)^* R_0^* (I - (P^*T_0)),$$

where $$R_0 = (R_E(n) + \alpha R_A(n))^{-1},$$

$$T_0 = (P'^* R_0^* P)^{\beta_1 -1} * (P'^* R_0),$$

and

I is the identity matrix. Processor 105 selects the smallest suitable non-negative value for the parameter $\alpha$ by using an iterative search with the condition that:

$$Err = 100(F-T)^* R_A(n)^* (F-T)'/F^* R_A(n)^* F'$$

does not exceed the range of 0.9 to 1.1%.

Figure 21:
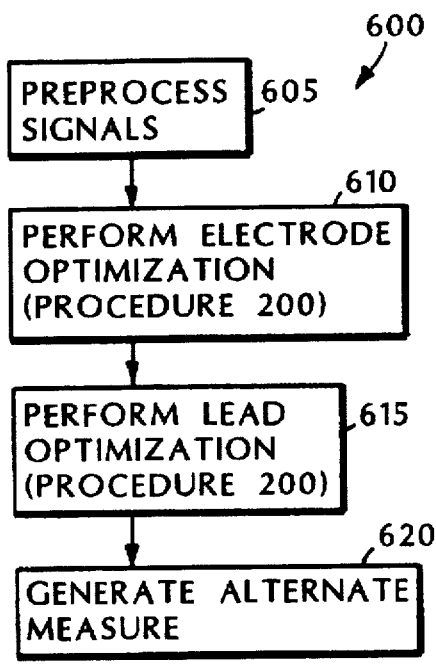
FIG. 21 is a flowchart of a procedure for producing an alternans measurement.

Referring to FIG. 21, processor 105 implements a two-stage noise-reduction procedure 600 to produce an alternans measurement based on signals from the entire electrode set illustrated in FIGS. 3 and 4. First, processor 105 preprocesses the input signals (step 605). Thereafter, processor 105 implements the first noise-reduction stage by performing electrode noise-reduction (step 610) to produce a set of twelve low-noise ECG signals (LA, LL, V1, V2, V3, V4, V5, V6, E, I, H and M). Processor 105 uses the twelve low-noise signals as input signals for the second noise-reduction stage. In the second noise-reduction stage, processor 105 performs noise-reduction (step 615) to produce a set of five low-noise signals (VM, X, Y, Z and V4). VM is a vector magnitude defined as:

$$VM = \sqrt{X^2 + Y^2 + Z^2}$$

Finally, processor 105 uses the five low-noise signals to produce an alternans measurement (step 620).

Processor 105 obtains thirty two signals from the fourteen electrodes illustrated in FIG. 3. Of the thirty two signals, there are twenty four ECG signals, seven electrode impedance signals, and one respiratory/transthoracic impedance signal. The impedance signals are produced using the current injection technique described above.

The twenty four ECG signals are named after their corresponding electrodes, with the name of the electrode referring to the center electrode of multi-segment electrodes and the suffix "a", "b", or "c" referring to signals from the ring segments of multi-segment electrodes. For most of the multi-segment electrodes, two or three of the outer ring segments are joined together to form a larger segment, which reduces the number of ECG signals that need to be recorded. All the of ECG signals are recorded relative to the average of the voltages at the RA, LA, and LL electrodes. This average is commonly referred to as the Wilson's central terminal.

The seven impedance signals measure the center segment impedances of the seven multi-segment electrodes. The impedance signals are named according to their corresponding electrode followed by the suffix "i".

As previously discussed, the respiratory signal (Resp) is a measure of the impedance of the patient's chest from the right side to the left side. Because air does not conduct electricity as well as body tissues do, the impedance across the chest changes as the lungs inflate and deflate due to respiration. Respiration also introduces baseline noise due to expansion and compression of the electrodes and changes in the impedance between the heart and the body surface.

Figure 24:
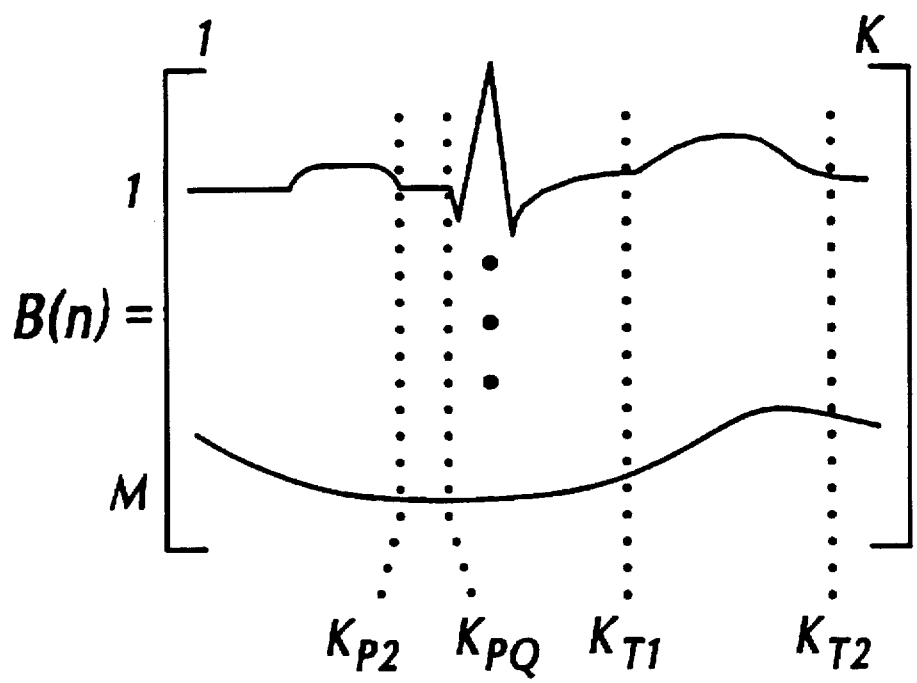
FIG. 24 is a matrix containing 32 input signals for a particular beat.
Figures 22, 23:
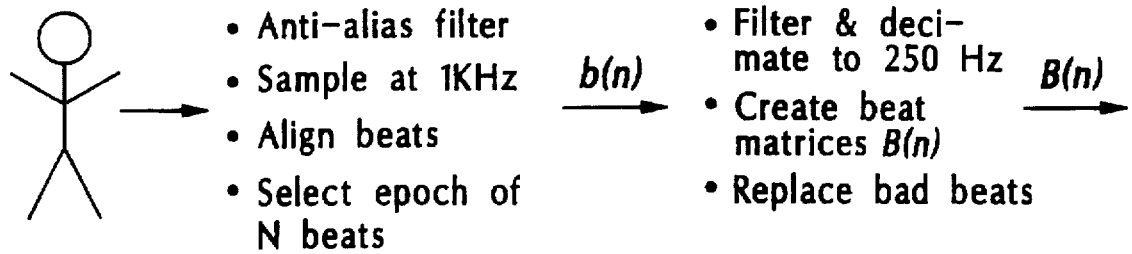
FIG. 22 is a diagrammatic view illustrating steps for preprocessing input signals.
FIG. 23 is a table defining signal elements of a $b(n)$ matrix.

The processor 105 preprocesses the signals (step 605) as illustrated in FIGS. 22-24. After amplifying and anti-alias filtering the signals, processor 105 digitizes the signals at a sampling rate of 1 kHz to create a 32 signal time series b(n). The contents of the rows of b(n) are shown in FIG. 23.

Next, processor 105 detects, aligns and classifies the beats within the time series b(n) to produce a series of beat matrices B(n). The processor 105 aligns each beat based on the QRS complex of the beat. Thereafter, processor 105 filters the beat and decimates the beat to 250 Hz around the alignment point. Finally, processor 105 stores the beat in a beat matrix B(n). The decimation allows for some data reduction and lowers the data storage requirements.

The structure of B(n) is shown in FIG. 24. Row m of B(n) corresponds to row m of b(n). The columns of B(n) correspond to successive digital samples over the duration of the beat. The samples start before the beginning of the P wave and end after the T wave. The indices $K_{P2}$ and $K_{PQ}$ delineate the PR interval while the indices $K_{T1}$ and $K_{T2}$ delineate the T wave.

During preprocessing, processor 105 also accounts for matrices corresponding to bad or abnormal beats. Grossly abnormal waveforms, such as premature atrial and ventricular beats, disrupt the subtle temporal pattern of beat-of-beat variability in waveform morphology that is indicative of alternans.

Abnormal beats may be identified by determining if their morphology differs from the normal waveform morphology by more than a predetermined threshold or if the preceding intercycle interval differs from the mean intercycle interval by more than some predetermined threshold.

Processor 105 can account for matrices that correspond to abnormal beats in a number of ways. In a first approach, processor 105 could simply eliminate the abnormal matrices from the sequence of beats. In another approach, processor 105 could replace the beat matrix corresponding to an abnormal beat with a matrix corresponding to a mean normal beat. In yet another approach, processor 105 could separately analyze each sequence of normal beats between abnormal beats and combine the analyses.

After preprocessing the signals (step 605), the processor 105 performs electrode noise-reduction (step 610). In particular, processor 105 performs electrode noise-reduction according to procedure 200 (FIG. 5) for each of the twelve low-noise ECG signals that are produced in this stage. Five of the twelve low-noise ECG signals (LA, V1, V2, V3, V5) correspond to standard electrodes. For each of these signals, processor 105 performs procedure 200 using a beat matrix B(n) that has nine rows, with the first row corresponding to the signal to be processed and the remaining rows corresponding to the eight impedance signals (LLi, V4i, V6i, Ii, Hi, Ei, Mi and Resp) (see FIG. 23). The other seven low-noise ECG signals (LL, V4, V6, E, I, H and M) correspond to multi-segment electrodes. For each of these signals, processor 105 performs procedure 200 using a beat matrix B(n) that includes a row corresponding to each signal of the electrode and eight rows corresponding to the impedance signals. Thus, for example, the beat matrix B(n) for V6 would include eleven rows, with the first three rows corresponding to V6, V6a and V6b, and the remaining eight rows corresponding to the impedance signals.

Processor 105 generates the low-noise output signals based on a neighborhood of thirty two beats in a manner identical to that described above for the generation of a low-noise X lead. In addition, processor 105 imposes a 1% morphology constraint. Thus, processor 105 selects the parameter α using an iterative search so that the Err function does not exceed 0.9 to 1.1%. This procedure is referred to as "adaptive noise-reduction" because the T matrices are continually adapted on a beat-to-beat basis.

Next, processor 105 performs noise-reduction using the twelve low-noise ECG signals (step 615) to produce low-noise X, Y, Z and V4 output signals. The X, Y, and Z vector signals have the advantage that the vector magnitude (VM) computed from these signals is immune to any alternans artifact created by rotation of the heart. The V4 signal is representative of the V1-V6 signals, which are known to contain information that is not present in the X, Y and Z signals.

FIG. 25 shows the how the X, Y, Z and V4 output signals are defined in terms of the input signals. The coefficients necessary to create the X, Y, Z, and V4 output signals are represented in the row vectors $F_X$, $F_Y$, $F_Z$, and $F_{V4}$. The low-noise output signals S(n) are represented as the matrix products of the F matrix with B(n).

Processor 105 performs noise-reduction every sixteen beats for a neighborhood of 128 beats. Thus, processor 105 performs noise-reduction for beats 1-128, 16-144, 32-160, etc.). For each group of 128 beats, processor 105 computes the matrices $T_X$, $T_Y$, $T_Z$ and $T_{V4}$ according to procedure 200. In performing the procedure 200, processor 105 implements the filter hl(n) as:

$$h_1(n) = 1/8 \, e^{i\pi k/4}, \text{ for } k = n-4 \text{ to } n+3,$$
$$= 0, \text{ otherwise.}$$

The frequency response of this filter is shown in FIG. 9C. Processor 105 implements filter $h_2(n)$ as a 128 beat average filter:

$$h_2(n) = 1/128 \text{ for } k = n-64 \text{ to } n+63,$$
$$= 0, \text{ otherwise.}$$

In addition, processor 105 imposes the geometry constraint and the 1% morphology constraint.

Once processor 105 generates the T matrices, it applies the T matrices to all 128 beats of a group. Note that a single beat (e.g., beat number 100) may appear in more than one group of 128 beats (e.g., 1-128 and 16-144) and have a different T matrix applied to it for the two different groups. This is referred to as "batch noise-reduction" because the same T matrix is applied to an entire batch of beats.

After optimizing X, Y, Z, and V4, processor 105 computes VM and the alternans measurement for each lead (step 620). Processor 105 then repeats the noise-reduction procedure for the next group of 128 beats (offset from the preceding group by sixteen beats). The sixteen beat offset is dictated by a desire to save computational time and resources, and can be adjusted as desired.

Figure 26A:
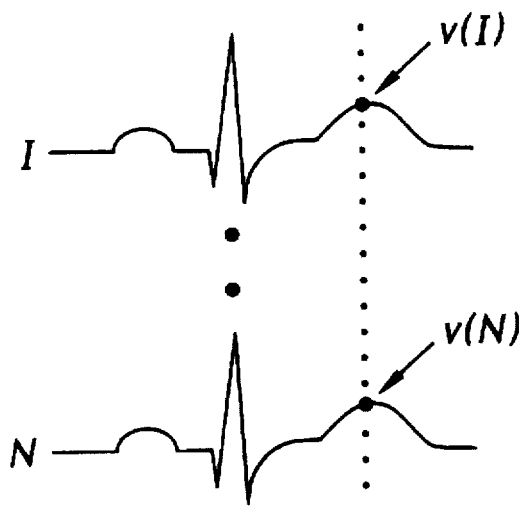
FIGS. 26A–26C are plots of physiologic signals over time.
Figure 26B:
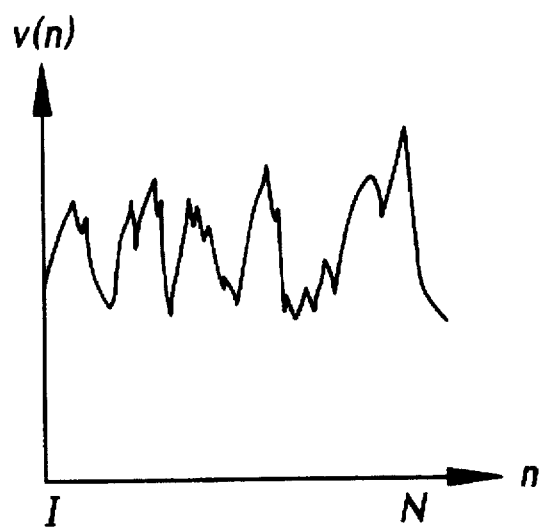
Figure 26C:
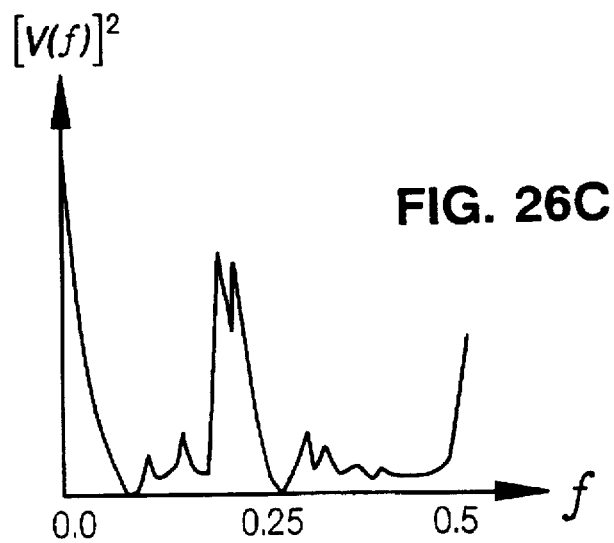

FIGS. 26A-26C summarize the method by which processor 105 computes the alternans measurement. First, processor 105 divides the T-wave region of the vector magnitude (VM) beats (FIG. 27A) into a column of points as represented by v(n) (FIG. 27B). Processor 105 then computes the power spectrum of v(n) is computed as V(f). The frequency corresponding to 0.5 cycles per beat is the alternans frequency. The power at the alternans frequency is denoted by $P_{0.5}$ and the noise in the reference band between 0.43 and 0.48 cycles/beat is denoted by $P_{noise}$ as described above. The level of alternans is considered significant if it exceeds the level of noise reference band by an amount equal to three standard deviations of the level in the reference band. The alternans in the X, Y, Z and V4 signals is computed using the same procedure as that used for computing the alternans of the vector magnitude signal VM.

Other embodiments are within the scope of the following claims. For example, the error signal has been defined above as the deviation in the isoelectric point from its mean value. The error signal could be defined on another part of the PQRST complex, such as, for example, the ST level in the region of the beat used for ST analysis or the T wave level in the region of the beat used for alternans analysis. The level may be relative to a reference feature of the ECG complexes or to a voltage level. The error signal could also be defined on an ECG signal from which has been subtracted the mean PQRST complex, or in terms of the beat-to-beat fluctuations in part or all of the PQRST complex. Similarly, the error signal could be derived from the beat-to-beat fluctuations in all or part of the PQRST complex, applying a different weight to fluctuations at different frequencies. The different frequencies could be weighed by filtering over multiple beats in the time range of the error signal used for the error metric.

The error metric could also be modified. In the described embodiment, the error metric is the mean squared value of the error signal and is computed over a neighborhood of beats. The error metric could also be defined as the output of a filter applied to the series of the error metrics of individual beats. Similarly, the error metric could be an aggregate metric that cannot be expressed as a simple combination of the metrics of individual beats. Model parameters that are computed on the basis of the error metric may be valid for a single beat, a small group of beats in the neighborhood of beats used to compute the error metric, or a large group of beats. In the event that the signals are considered over time instead of over the beats, the error metric could be defined as a filter applied over time. For example, a low pass filter could be applied to the output signal and the error metric could be defined as the energy of a signal produced by the filter.

In addition, while the described embodiment is directed to the processing of ECG signals, the described procedures could also be used to process other types of physiologic signals. Similarly, the procedures could be implemented without regard to the location of beats or without grouping signals into beats.

Also, while the described embodiment obtains physiologic signals using electrodes, signals could also be obtained using other types of sensors such as motion or pressure sensors. These signals could be used, for example, to supplement or replace the impedance signals.

What is claimed is:

1. A method of producing a measurement of alternans, comprising:

obtaining multiple input signals, at least one of which represents activity of a patient's heart;

determining a relationship between noise content of the input signals;

combining the input signals in consideration of the measured relationship to reduce effects of the noise content of the input signals and produce a measurement of alternans.

2. The method of claim 1, wherein the signal that represents activity of a patient's heart is obtained using an electrode and the multiple input signals include a secondary input signal that represents a property of the electrode.

3. The method of claim 2, wherein the property of the electrode represented by the secondary input signal comprises an impedance of the electrode.

4. The method of claim 1, wherein multiple input signals are obtained using segments of a multi-segment electrode.

5. The method of claim 1, wherein the multiple input signals include a secondary input signal that represents physical activity by a patient.

6. The method of claim 5, wherein the physical activity comprises motion of the patient.

7. The method of claim 6, wherein the secondary input signal is obtained using an electrode applied to the patient's skin and represents changes in electrical properties of an electrode-skin interface due to patient motion.

8. The method of claim 1, wherein the multiple input signals include a secondary input signal that is representative of respiratory activity of a patient.

9. A method of creating a noise-reduced result from an ECG signal, comprising:
obtaining multiple input signals that include one or more ECG input signals and one or more secondary input signals that represent noise;
dividing the one or more ECG input signals into sets of one or more points, wherein each set of points is synchronized to a beat of the ECG input signal;
dividing the one or more secondary input signals into sets of one or more points, wherein each set of points of the secondary input signal is synchronized with a corresponding set of points of the ECG input signal;
measuring a relationship between noise content of corresponding points from successive sets of points for the ECG input signal and the secondary input signal; and
combining the input signals in consideration of the measured relationship to produce a result having low noise content.

10. The method of claim 9, further comprising:
defining a desired result as a combination of one or more of the input signals;
modelling a low-noise result that approximates the desired result as a combination of two or more of the input signals, the model of the low-noise result including variable parameters that represent the relative contribution made to the low-noise result by each of the two or more input signals;
based on the relationship between noise content of the input signals, producing an error metric that represents noise content in the low-noise result, wherein the noise content in the low-noise result and a value of the error metric are affected by values assigned to the variable parameters of the model of the low-noise result; and
determining values of the variable parameters that cause the error metric to satisfy a predetermined condition;
wherein the step of combining comprises combining the input signals to produce the low-noise result using the determined values of the variable parameters.

11. The method of claim 10, wherein a first ECG input signal and a first secondary input signal are obtained using segments of a multi-segment electrode that is applied to a patient's skin.

12. The method of claim 11, wherein the step of modelling the low-noise result comprises modelling the low-noise result as a combination of at least the first ECG input signal and the first secondary input signal.

13. The method of claim 10, wherein the step of determining comprises determining values of the variable parameters that reduce the value of the error metric.

14. The method of claim 10, wherein the step of determining comprises determining values of the variable parameters that reduce the error metric while satisfying an additional condition.

15. The method of claim 14, wherein:
the combination of input signals that models the low-noise result includes the one or more input signals that define the desired result, and
the additional condition satisfied by the step of determining requires that a sum of the identified variable parameters associated with the one or more input signals that define the desired result equals a sum of parameters associated with the desired result.

16. The method of claim 14, wherein:
the desired result represents a physiologic signal sensed at a first location that is remote from a signal source, the first location being identified relative to the signal source by a first vector;
at least two of the input signals represent the physiologic signal;
each input signal that represents the physiologic signal represents the physiologic signal as sensed at a location corresponding to that input signal, the location being remote from the signal source and identified relative to the signal source by a corresponding vector; and
the additional condition satisfied by the step of determining requires that a sum of the vectors corresponding to the input signals that represent the physiologic signals, with each vector being weighted by the identified variable parameter associated with the corresponding input signal, equals the first vector.

17. The method of claim 10, wherein the step of defining the desired result comprises defining the desired result as a linear combination of two or more of the input signals.

18. The method of claim 10, wherein the desired result and the low-noise result represent an ECG signal.

19. The method of claim 18, further comprising using the low-noise result in producing a measurement of alternans.

20. The method of claim 19, wherein at least a first input signal of the multiple input signals is obtained using an electrode applied to a patient's skin, and wherein the multiple input signals include a second input signal that represents an impedance of the electrode.

21. The method of claim 20, wherein the step of modelling the low-noise result comprises modelling the low-noise result as a combination of at least the first and second input signals.

22. The method of claim 20, wherein the first input signal and at least a third input signal are obtained using segments of a multi-segment electrode.

23. The method of claim 22, wherein the step of modelling the low-noise result comprises modelling the low-noise result as a combination of at least the first, second and third input signals.

24. The method of claim 19, wherein at least a first input signal and a second input signal of the multiple input signals are obtained using segments of a multi-segment electrode that is applied to a patient's skin.

25. The method of claim 24, wherein the step of modelling the low-noise result comprises modelling the low-noise result as a combination of at least the first and second input signals.

26. The method of claim 9, wherein:
at least a first ECG input signal is obtained using an electrode applied to a patient's skin, and
at least a first secondary input signal represents an impedance associated with the electrode, and wherein the step of combining comprises combining the first ECG input signal and the first secondary input signal.

27. The method of claim 26, wherein the first ECG input signal and at least a third input signal are obtained using segments of a multi-segment electrode.

28. The method of claim 27, wherein the step of combining comprises combining the first ECG input signal, the first secondary input signal, and the third input signal.

29. The method of claim 9, wherein multiple input signals are obtained using segments of a multi-segment electrode.

30. The method of claim 9, wherein a secondary input signal represents physical activity by a patient.

31. The method of claim 30, wherein the physical activity comprises motion of the patient.

32. The method of claim 31, wherein the secondary input signal is obtained using an electrode applied to the patient's skin and represents changes in electrical properties of an electrode-skin interface due to patient motion.

33. The method of claim 9, wherein a secondary input signal represents respiratory activity of a patient.

34. The method of claim 9, wherein the step of combining comprises combining the input signals in consideration of the measured relationship to produce a measurement of alternans.

35. A method of creating a noise-reduced result, comprising:
measuring two or more primary input signals, each primary input signal representing activity of a patient's heart;
defining a desired result as a combination of the primary input signals;
measuring a secondary input signal that includes information about noise content in the desired result;
combining two or more of the primary input signals and the secondary input signal to produce a result that approximates the desired result and has reduced noise relative to the desired result.

36. The method of claim 35, wherein a primary input signal and the secondary input signal are obtained using segments of a multi-segment electrode.

37. The method of claim 36, wherein a primary input signal is obtained using an electrode and the secondary input signal represents a property of the electrode.

38. The method of claim 37, wherein the property of the electrode represented by the secondary input signal comprises an impedance of the electrode.

39. The method of claim 35, wherein the step of combining comprises combining the input signals to produce a measurement of alternans.

40. A method of creating a noise-reduced result, comprising:
measuring input signals that include primary input signals, each primary input signal representing activity of a patient's heart;
defining a desired result as a combination of one or more of the primary input signals;
measuring a relationship between noise content of the primary input signals; and
combining the primary input signals in view of the measured relationship to produce a result that has reduced noise relative to the desired result.

41. The method of claim 40, wherein:
the input signals include a secondary input signal related to noise, and
a primary input signal and the secondary input signal are obtained using segments of a multi-segment electrode.

42. The method of claim 40, wherein a primary input signal is obtained using an electrode and the input signals include a secondary input signal that represents a property of the electrode.

43. The method of claim 42, wherein the property of the electrode represented by the secondary input signal comprises an impedance of the electrode.

44. The method of claim 40, wherein the input signals include a secondary input signal that represents physical activity by the patient.

45. The method of claim 44, wherein the physical activity comprises motion of the patient.

46. The method of claim 45, wherein the secondary input signal is obtained using an electrode applied to the patient's skin and represents changes in electrical properties of an electrode-skin interface due to patient motion.

47. The method of claim 44, wherein the physical activity comprises respiratory activity of the patient.

48. The method of claim 44, wherein the primary input signal and the secondary input signal are obtained using segments of a multi-segment electrode.

49. A method of creating a low-noise result, comprising:
measuring one or more primary input signals that represent an ECG signal;
measuring one or more secondary input signals that represent noise in the ECG signal;
identifying one or more beats of the ECG signal;
determining parameters of the primary input signals and the secondary input signals for each identified beat of the ECG signal;
producing, based on the determined parameters, a noise metric that represents noise content in the low-noise result; and
combining the input signals in consideration of the noise metric to produce a result having low noise content.

50. A method of creating a noise-reduced result, comprising:
measuring input signals that include a primary input signal representing activity of a patient's heart and a secondary input signal that represents physical activity by the patient;
determining a relationship between noise content of the primary input signal and noise content of the secondary input signal; and
combining the primary input signal and the secondary input signal in consideration of the determined relationship to produce a noise-reduced result.

51. The method of claim 40, wherein the step of combining comprises combining the input signals to produce a measurement of alternans.

52. The method of claim 50, wherein the physical activity comprises motion of the patient.

53. The method of claim 50, wherein the secondary input signal is obtained using an electrode applied to the patient's skin and represents changes in electrical properties of an electrode-skin interface due to patient motion.

54. The method of claim 50, wherein the physical activity comprises respiratory activity of the patient.

55. The method of claim 50, wherein the primary input signal and the secondary input signal are obtained using segments of a multi-segment electrode.

56. The method of claim 50, wherein the step of combining comprises combining the input signals to produce a measurement of alternans.

57. The method of claim 50, wherein the primary input signal is obtained using an electrode and wherein a third input signal represents a property of the electrode.

58. The method of claim 57, wherein the property of the electrode represented by the third input signal comprises an impedance of the electrode.

* * * * *

UNITED STATES PATENT AND TRADEMARK OFFICE
CERTIFICATE OF CORRECTION

PATENT NO. : 5,704,365

DATED : January 6, 1998

INVENTOR(S) : Paul Albrecht, Jeffrey M. Arnold, Neil Judell, and Richard J. Cohen It is certified that error appears in the above-identified patent and that said Letters Patent is hereby corrected as shown below:

Cover page 2, [56] References Cited, OTHER PUBLICATIONS, the second "Adam et al." reference, "T-Wae" should be --T-Wave--.

Col. 5, line 21, the second occurrence of "is" should be --it--.

Col. 11, line 13, "100" should be --110--.

Col. 16, line 18, after "may" insert --be--.

Col. 19, line 60, "$E_{ET}(n)$" should be --$E_{TS}(n)$--.

Col. 20, the equation at line 2,
"$= (tr[T*R_e(n)*T+\alpha(F-T)*R_A(n)*(F-T)']$" should be
--$= tr[T*R_E(n)*T'+\alpha(F-T)*R_A(n)*(F-T)']$--.

Col. 21, line 46, "$(V_{ZLL})$" should be --$(V_{ZLL1})$--.

Col. 24, line 1, "$(Z_{V6C}, Z_{IC})$" should be
--$(Z_{V6R}, Z_{IC})$--.

Col. 25, line 9, "XZ+" should be --XI+--.

Col. 25, equation at line 40, "$F_x=[1000-100000]$" should be --$F_x=[1000-1000000]$--.

UNITED STATES PATENT AND TRADEMARK OFFICE
CERTIFICATE OF CORRECTION

PATENT NO. : 5,704,365
DATED : January 6, 1998
INVENTOR(S) : Paul Albrecht, Jeffrey M. Arnold, Neil Judell, and Richard J. Cohen It is certified that error appears in the above-identified patent and that said Letters Patent is hereby corrected as shown below:

Col. 25, equation at line 55,

" $P = \begin{bmatrix} 0000111111000 \\ 111100000000 \end{bmatrix}^1$ "

should be

-- $P = \begin{bmatrix} 000011111000 \\ 111110000000 \end{bmatrix}^1$ --.

Col. 26, equation at line 37, "$T_o = ('*R_o*P)^{-1}*(P'*R_o)$" should be -- $T_o = (P'*R_o*P)^{-1}*(P'*R_o)$ --.

Col. 27, equation at line 14, "$T_o = (P'*R_o*P)^{31\ 1}*(P'*R_o)$" should be -- $T_o = (P'*R_o*P)^{-1\ 1}*(P'*R_o)$ --.

Col. 29, line 29, "hl(n)" should be -- $h_1(n)$ --.

Signed and Sealed this

Eighth Day of September, 1998

Attest:

Attesting Officer

BRUCE LEHMAN
Commissioner of Patents and Trademarks